US006482837B1

(12) United States Patent
Wood

(10) Patent No.: US 6,482,837 B1
(45) Date of Patent: Nov. 19, 2002

(54) ANTIMUSCARINIC COMPOUNDS AND METHODS FOR TREATMENT OF BLADDER DISEASES

(75) Inventor: Ronald W. Wood, Rochester, NY (US)

(73) Assignee: University of Rochester, Rochester, NY (US)

( * ) Notice: Subject to any disclaimer, the term of this patent is extended or adjusted under 35 U.S.C. 154(b) by 0 days.

(21) Appl. No.: 09/298,146

(22) Filed: Apr. 23, 1999

Related U.S. Application Data

(60) Provisional application No. 60/083,043, filed on Apr. 24, 1998.

(51) Int. Cl.[7] .................. A61K 31/445; A61K 31/44

(52) U.S. Cl. .................. 514/315; 514/305; 514/281; 514/345; 514/346; 514/347

(58) Field of Search .................. 514/315, 305, 514/281, 345, 346, 347

(56) References Cited

U.S. PATENT DOCUMENTS

| | | | | |
|---|---|---|---|---|
| 2,648,667 | A | | 8/1953 | Sternbach .................. 546/137 |
| 4,467,095 | A | * | 8/1984 | Treves et al. .................. 546/342 |
| 5,001,160 | A | | 3/1991 | MacPherson et al. ....... 514/255 |
| 5,552,407 | A | | 9/1996 | Wood et al. .................. 514/291 |
| 5,821,249 | A | | 10/1998 | Wood et al. .................. 514/291 |

FOREIGN PATENT DOCUMENTS

| | | | |
|---|---|---|---|
| WO | 98/00133 | * | 1/1998 |
| WO | 9800138 | * | 1/1998 |

OTHER PUBLICATIONS

Pietzko et al. "Influences of trospium chloride and oxybutynin on quantitative EEG in healthy volunteers" Eur. J. Clin. Pharmacol. 1994, 47(4), 337–43 ISSN: 0031–6970.*
Sternbach et al., "Antispasmodics. I. Bicyclic Basic Alcohols," *J. Amer. Chem. Soc.* 74:2215–2218 (1952).
Abood, "The Psychotomimetic Glycolate Esters," in Burger, ed., *Drugs Affecting the Central Nervous System*, vol. 2, Chapter 4, New York: Marcel Dekker, Inc., pp. 127–167 (1968).
Baumgold et al., "Chemical Factors Influencing the Psychotomimetic Potency of Glycolate Esters," *Life Sciences* 17:603–612 (1975).
Deckers, "The Chemistry of New Derivatives of Tropane Alkaloids and the Pharmacokinetics of a New Quarternary Compound," *Postgraduate Medical Journal* 51(Suppl. 7):76–81 (1975).
Baumgold et al., "Studies on the Relationship of Binding Affinity to Psychoactive and Anticholinergic Potency of a Group of Psychotomimetic Glycolates," *Brain Research* 124:331–340 (1977).

Gibson et al., "The Distribution of the Muscarinic Acetylcholine Receptor Antagonists, Quinuclidinyl Benzilate and Quinuclidinyl Benzilate Methiodide (both tritiated), in Rat, Guinea Pig, and Rabbit," *The Journal of Nuclear Medicine* 20(8):865–870 (1979).
Abood, "Anticholinergics," Chap 15 in *Psychotropic Agents, Part III: Alcohol and Psychomimetics, Psychotropic Effects of Central Acting Drugs*, F. Hoffmeister et al., eds., Springer–Verlag, Berlin (1982), pp. 331–347.
Rzeszotarski et al., "Analogues of 3–Quinuclidinyl Benzilate," *J. Med. Chem.* 25:1103–1106 (1982).
Newberry et al., "Pharmacological Differences Between Two Muscarinic Responses of the Rat Superior Cervical Ganglion In Vitro," *Br. J. Pharmac.* 92:817–826 (1987).
Bonner et al., "Identification of a Family of Muscarinic Acetylcholine Receptor Genes," *Science* 237:527–532, Erratum 1556, 1628 (1987).
Bonner et al., "Cloning and Expression of the Human and Rat m5 Muscarinic Acetylcholine Receptor Genes," *Neuron* 1:403–410 (1988).
Gordon et al., "Distance Geometry of α–Substituted 2,2–Diphenylpropionate Antimuscarinics," *Molecular Pharmacology* 36:766–772 (1989).
Gross, "Medical Intelligence Drug Therapy. Ipratropium Bromide," *The New England Journal of Medicine* 319:486–494 (1988).
Gearien, "Cholinergics, Acetylcholinesterases, and Antispasmodics," in Foye, ed., *Principles of Medicinal Chemistry*, Third Edition, Philadelphia, Pennsylvania: Lea & Febiger, pp. 323–341 (1989).
Martin et al., "Pyrolysis and Volatilization of Cocaine," *Journal of Analytical Toxicology* 13:158–162 (1989).
Buckley et al., "Antagonist Binding Properties of Five Cloned Muscarinic Receptors Expressed in CHO–K1 Cells," *Molecular Pharmacology* 35:469–476 (1989).
Cereda et al., "Synthesis and Biological Evaluation of New Antimuscarinic Compounds with Amidine Basic Centers. A Useful Bioisosteric Replacement of Classical Cationic Heads," *J. Med. Chem.* 33:2108–2113 (1990).
Langtry et al., "Teordiline. A Review of its Pharmacological Properties, and Therapeutic Use in the Treatment of Urinary Incontinence," *Drugs* 40(5):748–761 (1990).
Roberts et al., "A Pharmacological Study of the Responses Induced by Muscarinic Agonists on the Isolated Superior Cervical Ganglion of the Guinea Pig," *European Journal of Pharmacology* 186:257–265 (1990).

(List continued on next page.)

*Primary Examiner*—Theodore J. Criares
*Assistant Examiner*—Jennifer Kim
(74) *Attorney, Agent, or Firm*—Nixon Peabody LLP

(57) ABSTRACT

Compositions comprising antimuscarinic compounds that have been modified to render them substantially irreversible, such as by quaternization of the heterocyclic ring nitrogen, have improved properties when administered intravesically for treatment of bladder diseases, particularly urinary incontinence. Pharmaceutical compositions and methods of treatment using these improved compounds or improved routes of administration re disclosed.

16 Claims, 11 Drawing Sheets

OTHER PUBLICATIONS

Sethia et al., "An Animal Model of Non–Obstructive Bladder Instability," *The Journal of Urology* 143:1243–1246 (1990).

Peterson et al., "Mini–Pig Urinary Bladder Function: Comparisons of In Vitro Anticholinergic Responses and In Vivo Cystometry with Drugs Indicated for Urinary Incontinence," *J. Auton. Pharmac.* 10:65–73 (1990).

Delforge et al., "Noninvasive Quantification of Muscarinic Receptors In Vivo With Positron Emission Tomography in the Dog Heart," *Circulation* 82(4):1494–1504 (1990).

Carter et al., Analogues of Oxybutynin. Synthesis and Antimuscarinic and Bladder Activity of Some Substituted 7–Amino–1–hydroxy–5–heptyn–2–ones and Related Compounds, *J. Med. Chem.* 34:3065–3074 (1991).

Madersbacher et al., "Control of Detrusor Hyperreflexia by the Intravesical Instillation of Oxybutynine Hydrochloride," *Paraplegia* 29:84–90 (1991).

Greenfield et al., "The Use of Intravesical Oxybutynin Chloride in Children With Neurogenic Bladder," *The Journal of Urology* 146:532–534 (1991).

Parsons et al., "Epithelial Dysfunction in Nonbacterial Cystitis (Interstitial Cystitis)," *The Journal of Urology* 145:732–735 (1991).

Waelbroeck et al., "Binding Kinetics of Quinuclidinyl Benzilate and Methylquinuclidinyl Benzilate Enantiomers at Neuronal ($M_1$), Cardiac ($M_2$), Pancreatic ($M_3$) Muscarinic Receptors," *Molecular Pharmacology* 40:413–420 (1991).

Thomas et al., "Irreversible Effects of 4–Damp Mustard on Muscarinic Receptors In Vivo," *Proc. West Pharmacol. Soc.* 35:233–237 (1992).

Carroll et al,. "Probes for the Cocaine Receptor. Potentially Irreversible Ligands for Dopamine Transporter," *J. Med. Chem.* 35:1813–1817 (1992).

Comer et al., "Clocinnamox: A Novel, Systemically–Active, Irreversible Opioid Antagonist," *The Journal of Pharmacology and Experimental Therapeutics* 262(3):1051–1056 (1992).

Kaiser et al., "Synthesis and Antimuscarinic Properties of Some N–Substituted 5–(Aminomethyl)–3,3–diphenyl–2(3H)–Furnanones," *J. Med. Chem.* 35:4415–4424 (1992).

Goldstein et al., *Principles of Drug Action: The Basis of Pharmacology,* Second Edition, New York: John Wiley & Sons, pp. 22–32 (1974).

Davies et al., "Novel 2–Substituted Cocaine Analogs: Binding Properties at Dopamine Transport Sites in Rat Striatum," *European Journal of Pharmacology—Molecular Pharmacology Section* 244:93–97 (1993).

Delforge et al., "Quantification of Myocardial Muscarinic Receptors with PET in Humans," *The Journal of Nuclear Medicine* 34(6):981–991 (1993).

Kaiser et al., "Synthesis and Antimuscarinic Activity of Some 1–Cycloalkyl–1–Hydroxy–1–Phenyl–3–(4–Substituted Piperazinyl)–2–Propanones and Related Compounds," *J. Med. Chem.* 36:610–616 (1993).

Kondo et al., "A Study on the Affinities of Various Muscarinic Antagonists to the Human Detrusor Muscle," *J. Smooth Muscle Res.* 29:63–68 (1993) (abstract in English).

Nordvall et al., "Binding–Site Modeling of the Muscarinic m1 Receptor: A Combination of Homology–Based and Indirect Approaches," *J. Med. Chem.* 36:967–976 (1993).

Griffin et al., "Kinetics of Activation and In Vivo Muscarinic Receptor Binding of N–(2–Bromoethyl)–4–Piperidinyl Diphenylacetate: An Analog of 4–DAMP Mustard," *The Journal of Pharmacology and Experimental Therapeutics—* 266(1):301–305 (1993).

Sebastian et al., "14β–[(p–Nitrocinnamoyl)amino]morphinones, 14β–[(p–Nitrocinnamoyl)amino]–7,8–dihydromorphinones, and Their Codeinone Analogues: Synthesis and Receptor Activity," *J. Med. Chem.* 36:3154–3160 (1993).

Weese et al., "Intravesical Oxybutynin Chloride: Experience with 42 Patients," *Urology* 41:527–530 (1993).

Connor et al., "Early Cystometrograms Can Predict the Response to Intravesical Instillation of Oxybutynin Chloride in Myelomeningocele Patients," *The Journal of Urology* 151:1045–1047 (1994).

Shishido et al., "Muscarinic Receptor Subtypes and Their Functional Roles in Rat Detrusor Muscle," $26^{th}$ Meeting of the International Continence Society, in *Neurourol. & Urodynamics* 15:313–314 (1996) (Abstract #36).

Guan et al., "A Minipig Model for Urodynamic Evaluation of Infravesical Obstruction and its Possible Reversibility," *The Journal of Urology* 154:580–586 (1995).

Kondo et al., "Muscarinic Cholinergic Receptor Subtypes in Human Detrusor Muscle Studied by Labeled and Nonlabeled Pirenzepine, AFDX–116 and 4DAMP," *Urol. Int.* 54:150–153 (1995).

Ehlert et al., "The Quarternary Transformation Products of N–(3–Chloropropyl)–4–Piperidinyl Diphenylacetate and N–(2–Chloroethyl)–4–Piperidinyl Diphenylacetate (4–DAMP Mustard) Have Differential Affinity for Subtypes of the Muscarinic Receptor," *The Journal of Pharmacology and Experimental Therapeutics* 276(2):405–410 (1996).

Krishnan et al., "A Double–Blind, Randomized, Placebo Controlled, Parallel Group, Multicentre Study of Intravesical Oxybutynin," *Neurol. & Urodynamics* 15:307–308 (1996) (Abstract #32).

Brown, "Atropine, Scopolamine, and Related Antimuscarinic Drugs," in Goodman et al., eds., *The Pharmacological Basis of Therapeutics,* Eighth Edition, New York: Macmillan Publishing Co., pp. 150–165 (1990).

Thuroff et al., "Randomized, Double–Blind, Multicenter Trial on Treatment of Frequency, Urgency and Incontinence Related To Detrusor Hyperactivity: Oxybutynin Versus Propantheline Versus Placebo," *The Journal of Urology* 145:813–817 (1991).

* cited by examiner

SUBSTITUTED 3-QUINUCLIDINIUM

METHYL QNB

SUBSTITUTED N-METHYL-3-PIPERIDINIUM

SUBSTITUTED N-METHYL-4-PIPERIDINIUM

SUBSTITUTED N-METHYL-3-PYRROLIDINIUM

SUBSTITUTED N-METHYL-3-GRANATANIUM

SUBSTITUTED N-METHYL-3-TROPINIUM

SUBSTITUTED QUATERNARY ATROPINE

SUBSTITUTED QUATERNARY ATROPINE EPOXIDE

SUBSTITUTED QUATERNARY ANHYDROECGONINE ESTER

OXYBUTYNIN

QUATERNARY OXYBUTYNIN ANALOGUES

GLYCOLATE ESTERS OF HETEROCYCLIC AMINO ALCHOHOLS
(WHEN $R_1$ IS A N-CONTAINING HETEROCYCLE AND $R_2$ IS OH)

4-DAMP MUSTARD

N-(2-HALOETHYL)-4-PIPERIDINYL DIPHEYLACETATE
Z = HALO GROUP (PREFERABLY Cl OR Br)

ANTIMUSCARINIC COMPOUNDS AND METHODS FOR TREATMENT OF BLADDER DISEASES

This application claims benefit of Provisional Appln. No. 60/083,043 filed Apr. 24, 1998.

STATEMENT OF RIGHTS TO INVENTIONS MADE UNDER FEDERALLY SPONSORED RESEARCH

Part of the work leading to the present invention was sponsored by research grants from the National Institute of Drug Abuse and from the National Institute on Aging. The United States government therefore has certain rights in this invention.

BACKGROUND OF THE INVENTION

1. Field of the Invention

The invention in the field of medicinal chemistry, pharmacology and medicine, related to novel compounds, and derivatives of known compounds and methods for their use in the treatment of bladder disease, particularly urinary incontinence, by intravesical instillation.

2. Description of the Background Art

Urinary incontinence afflicts a large and diverse patient population. The United States Department of Health and Human Services Agency for Health Care Policy and Research (AHCPR) reviewed the literature on the incidence of urinary incontinence, the clinical, psychological, and social impact of the disorder, as well as monetary costs to society. *Clinical Practice Guideline for Urinary Incontinence in Adults* (AHCPR 92-0038, 1992; abbreviated "AHCPR 1992"). Estimates vary, but approximately 15% of a randomly selected group of women perceived urinary incontinence as a social or hygienic problem. For noninstitutionalized individuals older than 60, the prevalence ranges from 15 to 30%, with women having twice the prevalence of men. Among those identified, approximately 25% have daily or weekly episodes of incontinence. Among nursing facility residents, the incidence is 50% or greater, with episodes occurring more than once per day. The annual direct costs of care based on 1987 dollars was estimated as $7 billion in the community and $3.3 billion in nursing homes.

Anticholinergic Therapy and the Treatment of Urinary Incontinence

For a detailed description of anticholinergic agents and their use in treating various diseases, see: Faye, W. P., PRINCIPLES OF MEDICINAL CHEMISTRY, Lea and Fibiger, 1989, pp. 328–348; Gilman, A. G. et al., (eds), *THE PHARMACOLOGICAL BASIS OF THERAPEUTICS*, 8th Edition, Macmillan Publishing Co., New York, 1990, chapter 8, pp. 150–165, both of which references are hereby incorporated by reference herein).

Contraction of the bladder detrusor muscle is mediated by cholinergic muscarinic receptors. Muscarinic receptors are divisible into several subtypes which are distinguishable based on binding of selective ligands. These muscarinic receptor subtypes exist in differing concentrations in different tissues. The $M_3$ muscarinic receptors predominate in the detrusor muscle, having about a ten-fold greater density than $M_1$ or $M_2$ receptor subtypes (Kondo, S. et al., *Urol. Int* 54:150–153, 1995; Kondo, S. et al., *J. Smooth Muscle Res.* 29:63–68, 1993; Shishido, K. et al., 26th Meeting of the International Continence Society. *Neurourol and Urodynamics* 15:313–314, 1996 (Abstract #36)). The present invention targets these receptors by administration of novel antimuscarinic agents via a catheter to the bladder to attain prolonged maintenance of bladder control in otherwise incontinent patients.

The drug oxybutynin chloride (FIG. 1K) (4-diethylamino)-2-butynyl-α-cyclohexyl-α-hydroxybenzeneacetate HCl; trade name Ditropan®) is the current standard anticholinergic therapeutic agent for urinary incontinence. Relief of symptoms in neurogenic bladder disorders are thought to result from its combined anticholinergic, antispasmodic, and local anesthetic activities. The anticholinergic side-effects limit its acceptability to many patients. In fact, use of oral oxybutynin is frequently discontinued because of the unpleasantness of the side effects (Thuroff et al, *J. Urol.* 145:813–817, 1991).

For treatment of detrusor overactivity, AHCPR 1992 (since reissued with minor revisions) recommended oxybutynin at oral doses of 2.5–5 mg, to be taken 3–4 times per day. At the time of agency review, 5 of 6 randomized controlled studies had reported superiority of oxybutynin to placebo. One exception was a study of elderly nursing home residents which used less frequent administration of the drug.

The dose-related anticholinergic side effects of oral oxybutynin include marked xerostomia, dry skin, blurred vision, nausea, and constipation. Severe mouth dryness occurred in 84% of subjects receiving 5 mg/kg four times/day (AHCPR, 1992). Side effects could be minimized by administration of this compound via clean intermittent self-catheterization directly into the bladder (intravesical administration). However, this required at least daily self-catheterization. Better restoration of bladder control required multiple catheter insertions each day. A series of papers reported beneficial effects in different patient groups. The following are representative: Brendler, *J. Urol.* 141:1350–1352, 1989; Weese, D. L. et al., *Urology* 41:527–530, 1993; Greenfield, S. P. et al., *J. Urol.* 146:532–534, 1991; Madersbacher, M. et al., *Paraplegia* 29:84–90, 1991).

A double-blind, randomized, placebo-controlled, parallel group study of intravesical oxybutynin was reported at a recent conference (Krishnan, K. R., *Neurourol and Urodyn.* 15:307–308, 1996). There was some systemic absorption of the drug following intravesical administration, but the incidence of adverse side effects was low. However, the difficulty in patients being able to continue a typical intravesical instillation protocol is illustrated by Weese et al. (supra), which reported that instillation of the drug two to three times daily via clean self intermittent catheterization resulted in 21% of the patients dropping out due to inability to tolerate the catheterization or to difficulty in retaining the drug solution in the bladder.

McPherson et al. (U.S. Pat. No. 5,001,160) described antimuscarinic agents for the treatment of neurogenic bladder disease. The compounds disclosed were said to have longer durations of action than did older anticholinergic agents such as methantheline and propantheline. The majority of neurogenic bladder patients have spastic or hypertonic conditions. Clinicians generally aim to convert this condition to hypotonia as a way to treat the primary problem of incontinence. Thus, when the condition has been "converted" to hypotonia, it can be managed in a straightforward way by intermittent catheterization. For those patients who cannot be converted from the hypertonic to the hypotonic state and who still need to urinate every hour, longer term treatment with an anticholinergic drug (muscarinic receptor antagonists) was said to be necessary. As noted above, the current drug of choice for this treatment is oxybutynin which is considered to be better than the older anticholinergics. McPherson et al. (supra) disclosed 1-aryl-1-hydroxy-1-$R_1$-3-(4-$R_2$-1-piperazinyl)-2-propanones. In preferred compounds, $R_1$ was a cycloalkyl of 3–6 carbons, most preferably cyclohexyl or cyclobutyl. $R_2$ was lower alkyl, benzyl, para-substituted benzyl or cinnamyl. The most preferred compound was 1-cyclobutyl-1-hydroxy-1-phenyl-3-(4-benzyl-1-piperazinyl)-2-propanone. For parenteral administration, the compounds were prepared in conventional aqueous injection solutions. This document disclosed that extemporaneous injection solutions could be prepared from sterile pills, granules or tablets and contained diluents, dispersing and surface active agents, binders and lubricants as well as the anticholinergic compound.

Tolterodine is a new antimuscarinic of comparable duration of action which is reported to cause a lower incidence of dry mouth (~9%). The following dose-related side effects were observed with tolterodine: diminished stimulated salivation after 3.2 mg, increased heart rate after 6.4 mg, and altered the nearpoint of vision after 12.8 mg. Six of 8 subjects reported micturition difficulties after a dose of 12.8 mg Other Drugs in the Treatment of Urinary Incontinence Terodiline has both anticholinergic and calcium antagonist properties, and effectively reduces abnormal bladder contractions caused by detrusor instability (Langtry, HD et al., *Drugs* 40:748–761 (1990)). When administered to adult patients with urge incontinence (generally as a 25 mg dose twice daily), terodiline reduced micturition frequency and incontinence episodes. Bladder volume at first urge and bladder capacity were increased. Children with diurnal enuresis respond similarly to a daily 25 mg dose. Terodiline at 50 mg/day was said to be preferred by patients when compared with emepronium 600 mg/day or flavoxate 600 mg/day, and tended to reduce voluntary micturition frequency and episodes of incontinence more effectively than these other drugs. Anticholinergic side effects were the most common ones reported.

Anhydroecgonine Derivatives as Anticholinergic Agents

Anhydroecgonine methyl ester (AEME), the primary pyrolysis product of cocaine, (B. R. Martin et al., *J. Anal. Toxicol.* 13:158 (1989)) is structurally similar to arecoline and anatoxin A. See FIG. 1J for a general structure of AEME compounds. While investigating the effects of crack smoking, the present inventor and his colleagues noted that experimental animals frequently showed bronchoconstriction. This observation led the inventors to focus on AEME and other anhydroecgonine esters (AEE) as bronchoconstrictors when given by inhalation. The present inventor initially studied this agent in isolated guinea pig tracheal rings and found, unexpectedly (in view of the bronchoconstricting action of cocaine), that AEME lacked cholinergic agonist activity. Even more surprisingly, AEME turned out to be a potent non-competitive muscarinic antagonist in vitro. The antagonistic effects were insurmountable by the addition of increasing amounts of acetylcholine (ACh). Furthermore the anticholinergic effects were irreversible, so that tissue exposed to AEME could not later attain its original magnitude of contraction. These findings were unexpected because AEME, resembling arecoline and anatoxin in structure, should have behaved as a cholinergic agonist. The present inventor and his colleagues described AEE compositions, derivatives or analogues thereof having anticholinergic activity, methods of preventing or inhibiting cholinergic responses and methods of using the compositions to prevent or treat diseases associated with bronchoconstriction (U.S. Pat. No. 5,552,407 and co-pending application U.S. Ser. No. 08/706,105 filed Aug. 30, 1996 (allowed), hereby incorporated by reference in their entirety.

Other Bladder Diseases

Interstitial cystitis (IC), a syndrome occurring primarily in women, is characterized by urinary urgency and frequency, suprapubic pain and petechial bladder mucosal hemorrhages upon distention under general anesthesia. Almost 50% of IC patients also suffer from allergies and irritable bowel syndrome, all of which are exacerbated by stress. One of the prevailing theories to explain IC pathophysiology is the increased number of activated mast cells in the bladder. Mast cells mediate hypersensitivity reactions wherein they are triggered by immunoglobulin E (IgE) and antigen (allergen) to release numerous vasoactive and proinflammatory substances. Mast cells are found in juxtaposition to neurons and are also activated by direct nerve stimulation, as well as by ACh, neurotensin and substance P.

Targeting Parasympathetic Control of Organ Function

In addition to its role in bladder control, the parasympathetic nervous system plays a major role in regulating bronchomotor tone. Thus, lessons learned in the field of pulmonary medicine have assisted the present inventor in conceiving the invention disclosed herein. One drug used to treat respiratory disease such as asthma is the quaternary anticholinergic agent isopropylatropine bromide, also called ipratropium bromide (Atrovent®) (Gross, H. J., *New Eng. J. Med.* 319:486–494 (1988); Higgenbottam, T. W. et al., eds., *Postgrad. Med. J.* 63 (Suppl):1–93 (1987)). This agent, administered by inhalation, is poorly absorbed so that it exerts its effects primarily, and in a limited manner, on the internal surfaces of the lungs. Thus, a major advantage of ipratropium for respiratory therapy is the possibility of reaching elevated regional tissue (lung) concentrations with few systemic anticholinergic effects. Another advantage of ipratropium compared to other anti-asthmatic drugs is its duration of action. Its pharmacologic effect becomes maximal in about an hour, and persists for several hours. Partly based on the foregoing, the present inventor conceived of the types of compounds useful for long duration therapy of bladder disease.

Quinuclidinol Derivatives as Anticholinergic Agents

Quinuclidinyl benzilate (QNB; FIG. 1B)) is a well-known anticholinergic agent that was originally prepared by Sternbach and colleagues at Hoffman LaRoche in the 1950's (Sternbach et al., *J. Amer. Chem. Soc.* 74:2215–2218 and 2219–2221 (1952); U.S. Pat. No. 2,648,667). QNB was studied by the military due to its central psychotomimetic potency, as discussed below. The present invention includes novel quinuclidinol derivatives and methods for using them, as well as a new use for known quinuclidinol compounds in the treatment of bladder diseases.

Gibson, R. E., et al., *J. Nucl. Med.* 20:865–870 (1979) determined the distribution of [$^3$H] QNB and its methiodide salt in rat, guinea pig, and rabbit. Accumulation in the myocardium of up to 2% of the injected dose per gram of tissue was observed with both compounds, providing heart-to-blood ratios of ~30 and heart-to-lung ratios of ~4. The accumulation in the heart was blocked (89%) by preinjection of atropine. The distribution of tritium in the rabbit heart corresponds to the muscarinic receptor density as determined in vitro. Calculated theoretical maxima for the bound-to-free ratio, based on in vitro equilibrium of binding isotherms, were in reasonable agreement with the experimental results. Because of the high accumulation in the heart with low serum concentration, the authors concluded that the methiodide salt of QNB represents an ideal parent structure for the design of receptor binding γ-emitting radiopharmaceuticals for imaging of the myocardium.

Rzeszotarski, W. J., et al., *J. Med. Chem.* 25:1103–1106 (1982) measured the affinities of a number of synthetic QNB analogs to muscarinic receptors from rat or dog ventricular muscle. It was determined that the muscarinic receptor can, to a different degree, accommodate either a halogen in the ortho, meta, or para position of one phenyl ring or could accommodate replacement of one phenyl ring with an alkyl group. In vitro competition studies showed that the affinities lay within a 270-fold range in the series of compounds tested, from the highest affinity compound, 3-quinuclidinyl-α-hydroxy-α-cyclopentylphenyl acetate, to the lowest affinity compound, 3-quinuclidinyl-α-hydroxy-α-2-propargylphenyl acetate.

Waelbroeck, M. et al., *Molec. Pharmacol.* 40:413–420 (1991), analyzed the competition kinetics of QNB and QNB methiodide enantiomers on muscarinic binding sites of human MV-OK1 neuroblastoma cells (primarily $M_1$), rat cardiac (primarily $M_2$), and rat pancreas (primarily $M_3$). The association rate constants ($K_a$'s) of the four drugs depended on the receptor subtype and were lower with pancreatic than with cardiac or MV-OK1 binding sites. At each receptor subtype, there were no significant difference between the $K_a$ of the R- and S-enantiomers of either QNB or QNB methiodide. Receptor stereoselectivity, when present, was associated with differences in unlabeled drug $K_d$'s. The $K_d$'s varied much more than the $K_a$'s. Competition kinetic analysis was used to compare either (a) (R)-QNB dissociation from the three receptor subtypes (half-life, 77 min to>340 min; best fit, 40 days) or (b) dissociation of the four drugs from each receptor subtype, with half-lives varying from 1.4 min to 4 hr at $M_1$ receptors, 1.1 to 77 min at $M_2$ receptors and 3.5 min to>340 min at $M_3$ receptors.

In the treatment of bladder disease, there is clearly a need in the art for new agents with improved activity profiles in the same direction as those shown by ipratropium for asthma. Urinary incontinence in particular is in need of new methods of treatment. The present invention is addressed to this need.

Citation of the above documents is not intended as an admission that any of the foregoing is pertinent prior art. All statements as to the date or representation as to the contents of these documents is based on the information available to the applicant and does not constitute any admission as to the correctness of the dates or contents of these documents.

SUMMARY OF THE INVENTION

The administration of quaternary anticholinergic agents with prolonged duration of action via a catheter to the bladder results in prolonged maintenance of bladder control in otherwise incontinent patients. Agents with durations of action between a week and a month could be useful for a significant number of patients and perhaps reach distinct groups for whom no satisfactory treatment is currently available.

This invention is directed to methods, chemical compounds and pharmaceutical compositions. The invention includes within its scope compounds yet to be synthesized, and new uses and routes of administration for known compounds. Also included are special kits useful for preparing the drug for administration, for administering it, and for quantifying effectiveness of drug delivery for individual patients.

Thus methods of promoting bladder control in incontinence and other bladder diseases using such compounds constitute a key embodiment of this invention.

The invention provides a compound for treating bladder disease which has improved antimuscarinic activity in the bladder and blocks $M_3$ muscarinic receptors. The compound is preferably a derivative of an antimuscarinic molecule. Formulas for preferred families of compounds are shown in FIGS. 1A–1M. FIGS. 1A–1J and FIG. 1L are quaternary base compounds that are intended to be used as salts, e.g., acid addition salts. It will be understood that when a compound is a quaternary base, the composition to be administered for treatment will always be a salt thereof.

Preferred compounds include derivatives of the following compounds:

N-methyl-3-quinuclidine (FIG. 1A is a quaternary quinuclidinium base),

N-methyl-3-piperidine (FIG. 1C is a 3-piperidinium base),

N-methyl-4-piperidine (FIG. 1D is a 4-piperidinium base),

N-methyl-3-pyrrolidine (FIG. 1E is a pyrrolidinium base),

N-methyl-3-granatanine (FIG. 1F is a granatanium base) (the IUPAC name for N-methyl-3 granatanol is 9-methyl-9-azabicyclononan-3-ol)

N-methyl-3-tropine (FIG. 1G is a tropinium base), quaternary anhydroecgonine esters (FIG. 1J)

quaternary derivatives of oxybutynin (FIG. 1K and FIG. 1L),

4-DAMP mustards (FIG. 1N).

A generic class of compounds into which many of the foregoing families of compounds fit is the class: glycolate esters of heterocyclic amino alcohols. These are illustrated in FIG. 1M.

The present invention also provides a method for ameliorating bladder disease, preferably incontinence, in a subject, comprising administering to the subject an effective amount of the pharmaceutical compositions and compounds of the invention. The method is useful for treating any of a number of bladder diseases, including interstitial cystitis and bladder dysfunction associated with any of a number of neurologic diseases, particularly spinal cord injuries or diseases such as spina bifida and myelomeningocele.

The present invention is directed to a method for treating bladder disease in a subject, comprising administering to the bladder of the subject an effective amount of a composition that comprises a chemical compound having the following properties:

(a) binds selectively to muscarinic receptors in the bladder when compared to non-muscarinic receptors, or in another embodiment, is $M_3$ receptor subtype-selective;

(b) is a glycolate ester of a heterocyclic amino alcohol of the general formula

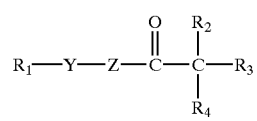

or a salt thereof, wherein $R_1$ is a heterocyclic N-substituted ring or a straight or branched alkyl, alkenyl or alkynyl chain that includes a N atom;

Y is a chemical bond or a lower alkyl group;

Z is O or S;

R$_2$ is OH, Cl, an acyl alcohol group or an acyl chloride group;

R$_3$ and R$_4$ are, independently, a substituted or unsubstituted phenyl, a substituted or unsubstituted cycloalkyl, a straight or branched chain alkyl, alkenyl or alkynyl, and further, one of R$_3$ and R$_4$ may be H.

The compound is delivered to the subject in the form of a pharmaceutical composition which includes a carrier or excipient appropriate for delivery to the bladder, such as a solution for intravesical instillation by catheterization.

Preferably, in this method, the N of R$_1$ is a quaternary N and R$_2$ is OH

In one embodiment, R$_1$ is a heterocyclic N-substituted ring, preferably one selected from the group consisting of 3-piperidinyl, 4-piperidinyl, 3-pyrrolidinyl, 3-quinuclidinyl, 3-granatanyl, 3-tropinyl, 3-granatanyl epoxide and 3-tropinyl epoxide.

When the N is quaternary, the N atom is preferably substituted with a straight or branched C$_1$–C$_{10}$ alkyl, alkenyl, alkynyl, substituted alkyl, substituted alkenyl, substituted alkynyl or an amidine. "Substituted" as used throughout includes aryl or heteroaryl substituents. In one embodiment, the quaternary nitrogen atom is substituted with methyl or isopropyl.

In one embodiment, the above method utilizes a compound wherein R$_1$ is an N-methyl quinuclidinyl ring; Y is a chemical bond Z is O; R$_2$ is OH; R$_3$ and 1R$_4$ are each phenyl. This compound is known as methyl QNB (see below). In another preferred method R$_1$ is a quinuclidinyl or N-methyl quinuclidinyl ring, Y is a chemical bond or CH$_2$; Z is O; R$_2$ is OH' and R$_3$ and R$_4$ are phenyl and cyclopentyl (See "compound 3167" discussed below). In a related embodiment, R$_1$ is an N-methyl-4- piperidyl ring, Y is a chemical bond or CH$_2$; Z is O; R$_2$ is OH; and R$_3$ and R$_4$ phenyl and cyclobutyl (see "compound 3580", below). In yet another embodiment, R$_1$ is an N-methyl-4-piperidyl ring; Y is a chemical bond or CH$_2$; Z is O; R$_2$ is OH; and R$_3$ and R$_4$ phenyl and cyclopentyl (see "compound 3443", below).

The present invention also provides a method as above, wherein R$_1$ is 4-piperidinyl in which the N is substituted with X'; R$_2$ and R$_4$ are phenyl; R$_3$ is H; X' is a lower alkyl group optionally halogenated. X is preferably bromoethyl or bromopropyl. In the above, method, the ring N may also be quaternized by substitution with a straight or branched C$_1$–C$_{10}$ alkyl, alkenyl, alkynyl, substituted alkyl, substituted alkenyl, substituted alkynyl or an amidine.

The present method also utilizes compounds wherein R$_1$ is a chain having the formula

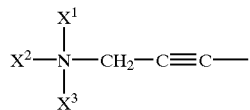

wherein X$^1$ and X$^2$ are lower alkyl, and X$^3$ is a straight or branched C$_1$–C$_{10}$ alkyl, alkenyl, alkynyl, substituted alkyl, substituted alkenyl, substituted alkynyl or an amidine. in a preferred embodiment, Y is a chemical bond, Z is O, R$_2$ is OH, R$_3$ and R$_4$ are any of phenyl, cyclohexyl or cyclopentyl, X$^1$ and X$^2$ are ethyl. These compounds are derivatives of oxybutynin.

The present method may also be carried out with a compound as described above, additionally substituted with a reactive or alkylating function on any one of R$_1$, R$_2$, R$_3$ or R$_4$. For example, when R$_1$ is a heterocyclic N-substituted ring, the reactive or alkylating function may be a substituent on the quaternary nitrogen group of the ring (as in a compound described above. In another embodiment, (i) R$_1$ is a heterocyclic N-substituted ring, and, (ii) a reactive substituent of a carbon atom of the ring, preferably in the para position relative to the N, spontaneously cyclizes in solution, thereby generating the alkylating function, for example, an aziridinium ion.

The foregoing methods are useful for treating any of number of bladder disease, but are particularly aimed at people suffering from urge incontinence or interstitial cystitis. The preferred route of administration is by intravesical instillation. This is preferably done at a lower frequency than once daily, preferably once weekly or even less.

The present invention also provides a composition useful for treating bladder disease in a subject, which comprises a chemical compound having the following properties:

(a) binds selectively to muscarinic receptors in the bladder when compared to non-muscarinic receptors, and, preferably is M$_3$ subtype-selective (b) upon intravesical instillation, suppresses the undesired symptoms of urge incontinence for a period of greater than six hours per dosing, as measured by reduction in (i) detrusor tone or (ii) frequency of micturition or in (iii) prolongation of void time. This duration of action is an important distinguishing feature of the present compounds over the prior art.

(c) is a glycolate ester of a heterocyclic amino alcohol, of the general formula

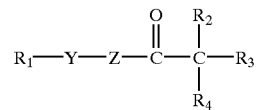

or a salt thereof, wherein

R$_1$ is (i) a heterocyclic N-substituted ring with a quaternary N atom, or (ii) a straight or branched alkyl, alkenyl or alkynyl chain that includes a quaternary N atom;

Y is a chemical bond or a lower alkyl group;

Z is O or S;

R$_2$ is OH, Cl, an acyl alcohol group or an acyl chloride group;

R$_3$ and R$_4$ are, independently, a substituted or unsubstituted phenyl, a substituted or unsubstituted cycloalkyl, a straight or branched chain alkyl, alkenyl or alkynyl, and further, one of R$_3$ and R$_4$ may be H.

with the proviso that said compound is not N-(2-chloroethyl)-4-piperidinyl diphenylacetate, N-(3-chloropropyl)-4-piperidinyl diphenylacetate, N-(2-bromoethyl)-4-piperidinyl diphenylacetate, methyl quinuclidinyl benzilate, methylatropine, methylscopolamine, isopropylatropine, homatropine methylbromide, methantheline bromide, propantheline bromide, anisotropine methylbromide, glycopyrrolate, hexocyclium methylsulfate, isopropamide, mepenzolate bromide, triihexaethylchloride (a number of which compounds are cited using their "pharmacological" rather than chemical name in Goodman and Gilman's *The Pharmacological Basis of Therapeutics*, 8$^{th}$ edition, Gilman et al., eds, 1990, Pergamon Press, New York.

In the above composition, R$_2$ is preferably OH. In another embodiment, R$_1$ is preferably a heterocyclic N-substituted ring, more preferably selected from the group consisting of 3-piperidinyl, 4-piperidinyl, 3-pyrrolidinyl, 3-quinuclidinyl, 3-granatanyl, 3-tropinyl, 3-granatanyl epoxide and 3-tropinyl epoxide.

The quaternary nitrogen atom, above is preferably substituted with a straight or branched $C_1$–$C_{10}$ alkyl, alkenyl, alkynyl, substituted alkyl, substituted alkenyl, substituted alkynyl or an amidine.

In another embodiment, the composition $R_1$ is 4-piperidinyl in which the N is substituted with X'; $R_2$ and $R_4$ are any of phenyl, cyclohexyl or cyclopentyl; and $R_3$ is H; wherein X is an optionally halogenated lower alkyl group, most preferably ethylbromide or isopropylbromide.

In another embodiment, $R_1$ above is a chain having the formula

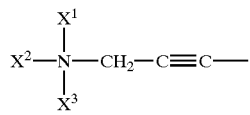

wherein $X^1$ and $X^2$ are lower alkyl, and $X^3$ is a straight or branched $C_1$–$C_{10}$ alkyl, alkenyl, alkynyl, substituted alkyl, substituted alkenyl, substituted alkynyl or an amidine.

In one embodiment, Y is a chemical bond, Z is O, $R_2$ is OH, $R_3$ and $R_4$ are any of phenyl, cyclohexyl or cyclopentyl, and $X^1$ and $X^2$ are ethyl.

Also included herein is a composition as above wherein said compound is additionally substituted with a reactive or alkylating function on any one of $R_1$, $R_2$, $R_3$ or $R_4$. When $R_1$ includes heterocyclic N-substituted ring, the reactive or alkylating function can be a substituent on the quaternary N of said ring. Alternatively, the reactive substituent is on a ring carbon atom and produces, by spontaneous cyclization in solution, the alkylating function. In a preferred composition, the alkylating moiety is an aziridinium ion.

Also provided herein is a pharmaceutical composition comprising a composition and above and a pharmaceutically acceptable excipient or carrier for intravesical administration.

In summary, the types of derivatives useful as compositions and in the methods of this invention are (i) a quaternary derivative of molecules of the families discussed above, (ii) a derivative modified to have increased molecular mass by addition of an organic chain including a glycosaminoglycan (GAG), or another moiety that is acceptable in the intravesical environment, to a site of the molecule without adversely affecting binding to muscarinic receptors, particularly of the $M_3$ subtype, or (iii) a derivative to which is added a reactive organic moiety, preferably a mustard group or other alkylating moiety, which renders the derivative capable of binding substantially irreversibly (see definitions, below) to a cell constituent in conjunction with binding of the compound to a bladder $M_3$ muscarinic receptor. Such additional binding may be to a transmembrane G protein, at an opening or on the cell surface.

One class of preferred compounds, which is a subgroup of molecules of FIG. 1G, is substituted quaternary atropines of FIG. 1H, wherein Z is a straight or branched $C_1$–$C_{10}$ alkyl, alkenyl, alkynyl, or an amidine; and at least one of $R_1$, $R_2$ and $R_3$ is an isothiocyanate, a thiocyanate, a fumaramate methyl ester, a carboxyl methyl ester, a p-azidophenylethylester, a p-isothiocyanatophenylethylester, a p(bromacetoamido)phenylethylester or a 3-iodo-4-azidophenylethylester. Another preferred compound is an epoxide of the substituted quaternary atropine, shown in FIG. 1I with preferred substituents as indicated above.

In another embodiment, the present invention is directed to a composition comprising AEME or a derivative or analogue thereof (FIG. 1J) having anticholinergic activity, which derivative or analogue has the additional property of irreversibility and long duration of action. Preferred compounds of this group have substantially irreversible antimuscarinic anticholinergic activity and derivatives of FIG. 1J wherein $R_2$ is H, $C_1$–$C_{10}$ alkyl, alkenyl, alkynyl or amidine, and $R_1$ is a reactive organic moiety capable of binding covalently to a constituent of the surface of a cell after the compound has bound to a muscarinic receptor on the cell surface. Preferred compounds of this class having irreversible antimuscarinic activity are selected from the group consisting of anhydroecgonine-2β-carboxylic acid-2-(p-azidophenyl)ethylester, anhydroecgonine-2β-carboxylic acid-2-(p-isothiocyanatophenyl)ethylester, anhydroecgonine-2β-carboxylic acid-2-[p(bromacetoamido)phenyl]ethylester, anhydroecgonine-2β-carboxylic acid-2-(3-iodo-4-azidophenyl)ethylester, anhydroecgonine-2β-isothiocyanate and anhydroecgonine-2β-thiocyanate. However, because of the relative irreversibility and long duration of action of AEME and other AEE's, this family of compounds may be used herein without the need for derivatizing with a mustard group or with another highly reactive group.

The present invention is further directed to a method of modifying an antimuscarinic compound to become a substantially irreversible inhibitor (see definitions), comprising modifying an antimuscarinic compound with a reactive organic moiety that is capable of binding covalently to a constituent of the surface of a cell after the compound has bound to a muscarinic receptor on the surface of the cell. The antimuscarinic compound so modified may be a member of any class of antimuscarinic compounds that binds to the $M_3$ receptor subtype. Examples include any compounds of FIGS. 1A–N which include antimuscarinic agents of the oxybutynin (FIG. 1K) family, generically described by the formula shown in FIG. 1L, or the 4-DAMP mustard (FIG. 1N) family. However, this invention includes any antimuscarinic agent that can be modified with such a reactive group while preserving its receptor binding and pharmacologic activity.

According to the present invention, these compounds are modified as described above to render them substantially irreversible, which term is defined below.

The present invention is also directed to a pharmaceutical composition useful for treating and inhibiting bladder disease, preferably incontinence, in a subject comprising (a) an antimuscarinic agent or a derivative or analogue thereof as described above; and (b) a pharmaceutically acceptable carrier or excipient for intravesical instillation. Preferred additions to such compositions are materials which enhance viscosity or promote the entry of the active agent into the bladder wall, such as carboxymethyl celluloses and, particularly, GAGs.

In a related embodiment, the treatment includes the physical or pharmacological creation of a depot/slow release compartment for the composition. This can be achieved, for example, by deliver of the agent using liposomes or othe known delivery agents having the noted action on release. Another approach comprises the use of protamine (or a protamine-like compound) to alter the surface of the bladder, thereby fostering access. Alternatively, to enhance access. The subject is first treated with protamine or a protamine-like agent is followed by administration of the active antimuscarinic agent in combination with a glycosamine. In yet another embodiment, the endogenous intravesical GAG compartment is exchanged with or replaced by an exogenously applied mixture that incorporates the antimuscarinic composition of this invention.

The present invention also provides a method for irreversibly inhibiting a muscarinic cholinergic response in urinary bladder cells, bladder tissue or the whole organ, comprising providing to the cells, tissue or organ an effective anticholinergic concentration of a composition as described herein.

Also provided are kits for administering the compositions, which comprise the antimuscarinic agent and the supplies that are needed to prepare the composition for intravesical administration and equipment for administering the composition.

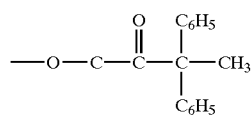

The model illustrates the approximately 5.2 Å bond distance between the protonated nitrogen shown interacting with the receptor's anionic site that may contain an aspartic acid residue, and the carbonyl oxygen, where the ester site of the antagonist could participate in hydrogen bonding with the receptor.

Figure 3B:
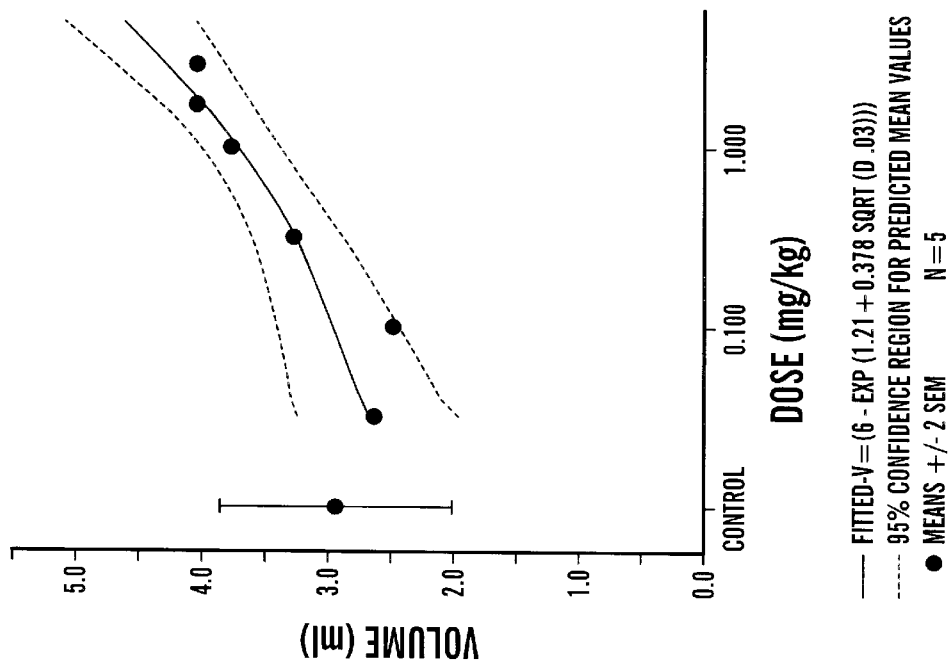
Figure 3A:
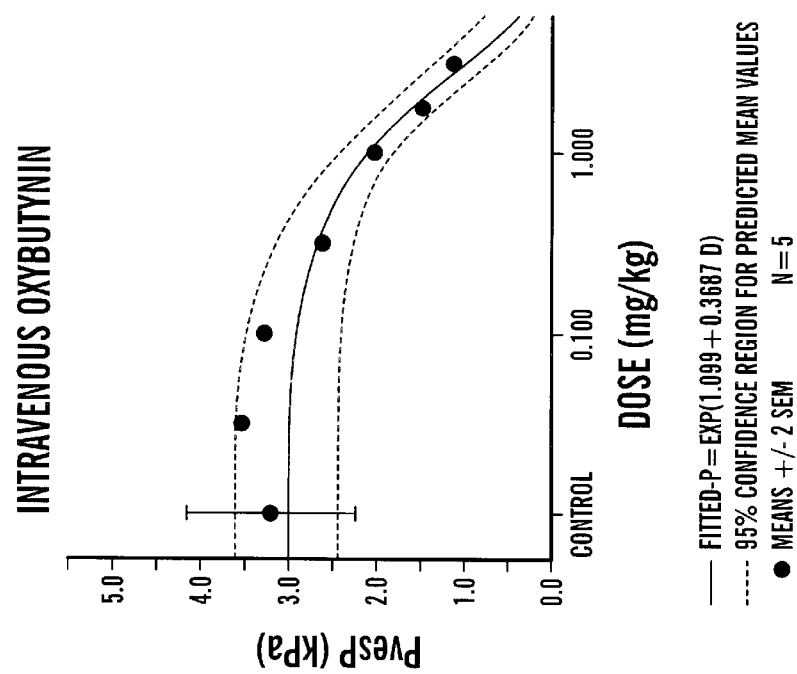

FIGS. 3A and 3B are a set of two graphs showing dose response curves of oxybutynin affecting peak intravesical pressure (FIG. 3A) and bladder volume (FIG. 3B) measured during cystometry of a urethane anesthetized guinea pig.

Figure 4:
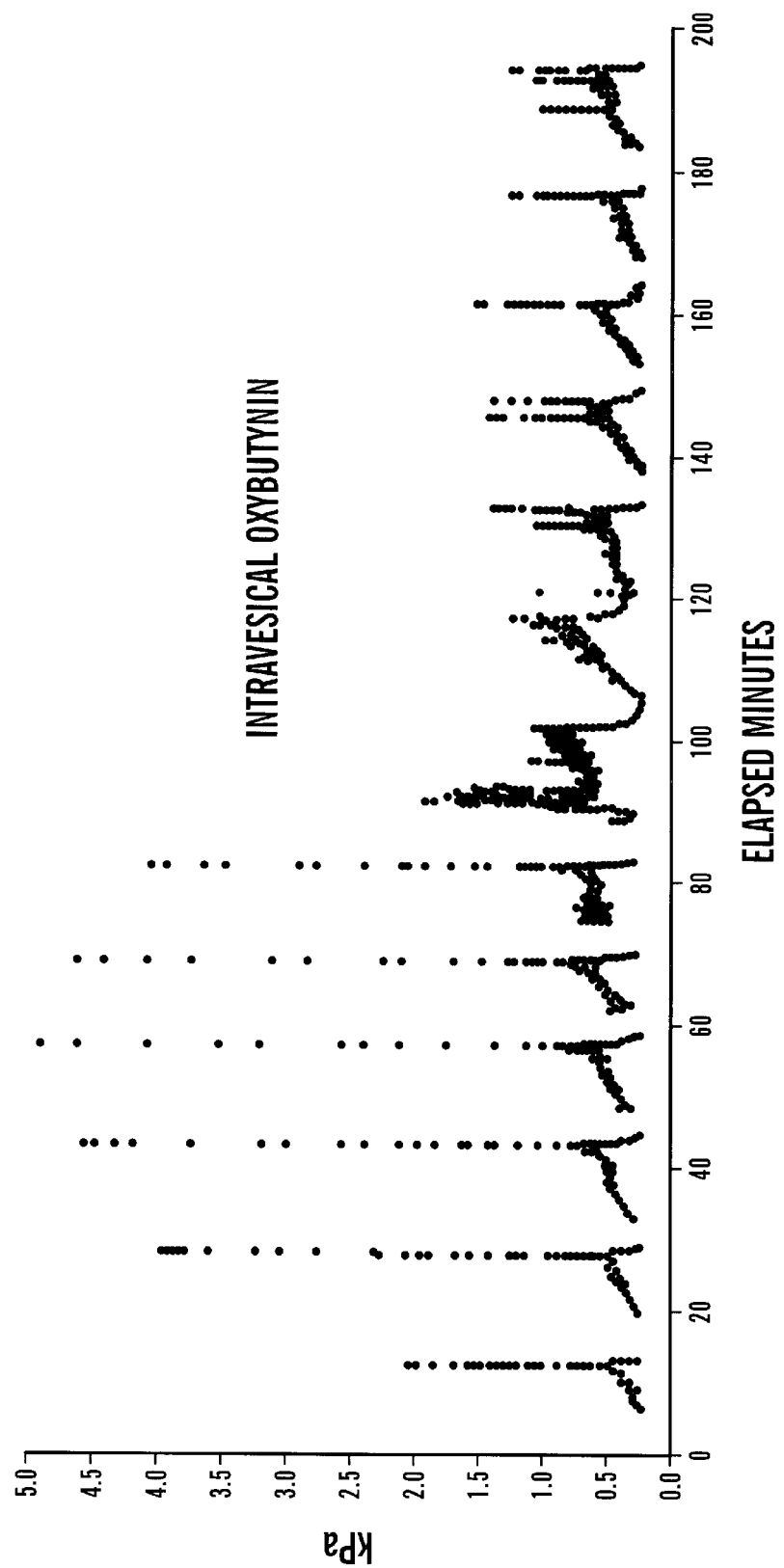

FIG. 4 is a cystometrogram showing the effect of oxybutynin ($10^{-3}$M) on peak intravesical pressure when administered intravesically at a rate of 0.5 ml/min.

FIGS. 5A–5E presents data collected from a typical miniature swine cystometry session. The top panel (5A) presents intravesicular ($P_{ves}$) and intraabdominal ($P_{abd}$) pressure, and the difference ($P_{det}$) between these two. (The right axis is for the intraabdominal pressure). The 10 mm Hg pressure event in the bladder at 11:30 was a true bladder contraction. The magnitude of the motion artifacts in $P_{det}$ are reduced in comparison to $P_{ves}$ as a result of subtracting $P_{abd}$. Panel 5B is the raw data signal from the transducer. Panel 5D displays the signal after noise filtering. Panel 5E shows the integrated total flow across the session. Panel 5C shows the skin and vaginal temperatures throughout the study. The drops in vaginal temperature represent the voiding of cooler saline into the vagina, providing additional verification as to when integrated urine volume estimates shown in Panel 5E are accurate.

Figure 6A:
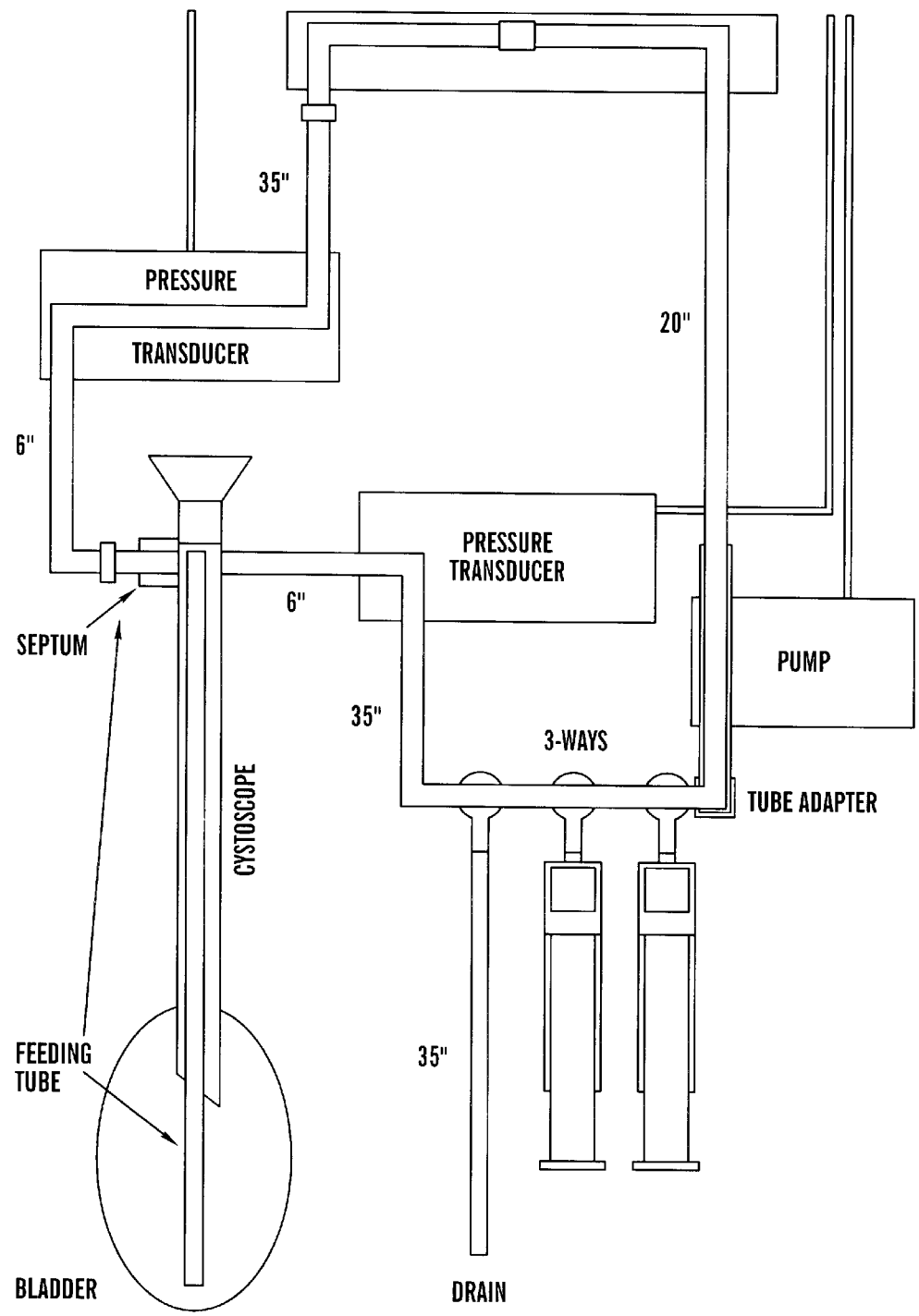
Figure 6B:
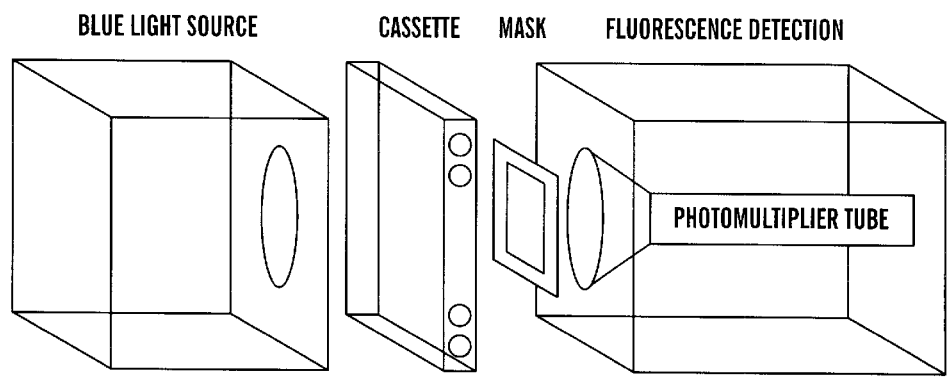
Figure 6C:
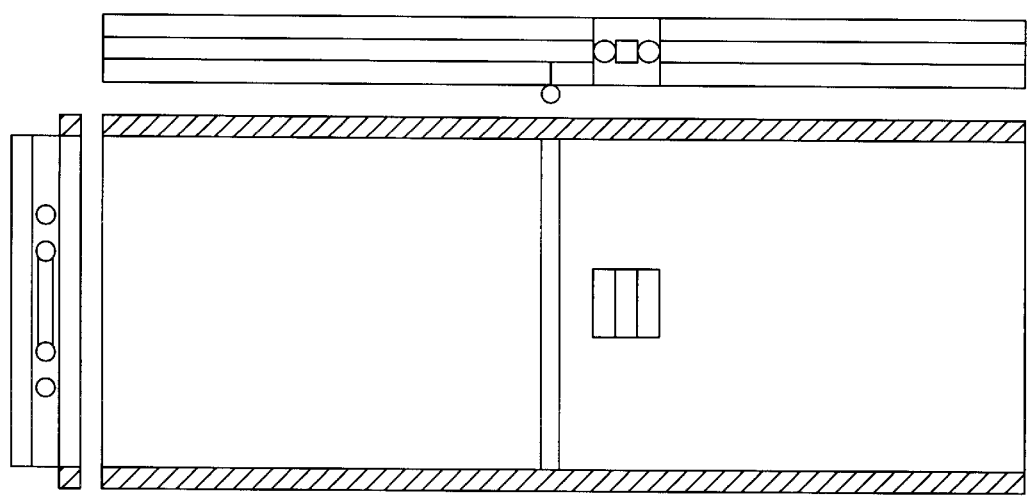

FIGS. 6A–6C shows an exploded diagram of a light-tight custom spectrofluorimeter (FIG. 6A) with a "slide-in" cassette for holding a "cuvette" and "standard calibration" tubing. The cassette opens on a hinge for insertion and removal of the extension tubing. The cassette is wider than the lightpath, and acts as a shutter for the photomultiplier tube when pulled into the loading position. The mask comprises the back wall of the cassette, and opens the photomultiplier tube to light excitation when the cassette is inserted into the spectrofluorimeter.

DESCRIPTION OF THE PREFERRED EMBODIMENTS

The present invention provides compositions and methods for the treatment of bladder disease (as defined below) by the delivery of agents to the bladder which bind in a substantially irreversible manner to the muscarinic cholinergic receptors (primarily $M_3$ receptors), resulting in more sustained anticholinergic effects than has previously been attained and with fewer side effects compared to systemic administration of such agents. These compositions and methods are particularly suitable for self-administration by patients.

Considering the spectrum of potential side-effects of agents with irreversible or very long duration activities, the prevention of central nervous system effects emerges as a significant priority, as one would not want a chronic impairment of memory or cognition in an elderly population. Thus quaternary amino compounds would emerge as the most preferred in this regard. Quaternary anticholinergic compounds have achieved clinical use to treat urge incontinence.

Quaternary compounds have long been used in experimental pharmacology to distinguish central from peripheral mechanisms of actions. For example, methylatropine and methylscopolamine retain their peripheral anticholinergic activites, but do not affect conditioned behaviors as effectively as do atropine or scopolamine molecules.

For use in accordance with this invention, the preferred antimuscarinic agent has (1) receptor-selective activity, and (2) the activity is of long duration in the target organ following local administration to an internal surface of that organ. An example from the art of treating asthma is the local application isopropylatropine to the inner surface of the lung. If the agent is not given in excess dosage, long duration side-effects should not occur. Quaternization does not eliminate peripheral activity; one of primary purposes of this chemical change is to prevent passage of the agent across the blood-brain barrier. To the present inventor's knowledge, there are no publications desribing the effect of quaternization of a compound administered intravesically on subsequent blood levels of the quatenary compound. There is an expectation of some systemic absorption. The main consequence of overdose via the intravesical route is most likely to be hypertonicity of the bladder detrusor muscle. This side effect would be counteracted by clean intermittent or subchronic catheterization until the effect diminishes. The present inventor does not expect significant peripheral side-effects in the presence of drug-induced detrusor hypertonicity. Nonetheless, chemical modifications of the antimuscarininc agent to exclude it from the central nervous system is desirable in the context of chronic use; if the usual anticholinergic peripheral side-effects did occur, they might be unpleasant but would not result in subtle or serious central nervous system impairment.

Definition of Terms

According to the present invention, a composition used to treat bladder disease is preferably substantially irreversible, meaning that it has a prolonged duration of action compared to a conventional muscarinic antagonist. This may be a result of covalent bonding to a receptor or another site of the cell, or because of a slow "off rate". The inventor does not intend this term to imply that one cannot measurable an "off rate" (as in the case of hydrolysis of a xenobiotic where the receptor is left in a free state. To be substantially irreversible as intended herein, a compound preferably has a duration of pharmacologic effect of at least 12 hours, more preferably at least 24 hours, more preferably at least 7 days, even more preferably at least about 3 weeks. The desired pharmacologic effect is that of increased residual bladder volume and/or reduced peak intravesical pressure, leading to the prevention of unwanted episodes of micturition. As is well-known in the pharmacologic arts, termination of an agent's action may result from a number of processes including tolerance of the subject, dissociation from the receptor, receptor upregulation, breakdown of the agent in situ and the associated return of the receptor to the functional population.

The criteria for the inclusion of a compound in the present invention are its ability to mimic the actions of an anticholinergic drug such as oxybutynin but with a longer duration of action. The compounds of this invention must have an action that results in one or, preferably, a combination, of the following outcomes: (1) decrease peak intravesical pressure during voiding; (2) increase bladder capacity; (3) increase the interval between voids. Furthermore, the compound should have few side effects and be well-tolerated by patients. Side effects are minimized in several ways, compared to drugs in the prior art. First, intravesical administration, the preferred route, itself results in fewer systemic effects than systemic administration of the drug. The presence of a quaternary nitrogen atom, a high degree of lipophilicity, a bulky side chain or other means for increasing the overall size and molecular mass of the pharmacologically active moiety, or a combination of these properties, minimizes entry into the CNS thereby avoiding a significant number of known side effects.

"Alkyl" means a branched or unbranched, saturated hydrocarbon chain containing 1–10 carbon atoms, such as methyl, ethyl, propyl, tert-butyl, n-hexyl and the like. "Optionally aryl substituted alkyl" means a moiety in which a substituted or unsubstituted phenyl or other aryl group (including a heterocyclic ring) may or may not be attached to a C, preferably the omega C of the alkyl group as defined herein.

As used herein, the term "bladder disease" is intended to encompass urinary incontinence such as that due to overactive detrusor function, either idiopathic detrusor instability or detrusor hyperreflexia. The condition may be neurogenic in origin, such as, for example, in spinal cord injury or myelomeningocele patients. Also intended is interstitial cystitis Any disease of the central and or peripheral nervous system that manifests bladder dysfunction, incontinence, spasticity, etc. can be treated by the compositions and methods disclosed herein.

By the term "treating" is intended the administering to subjects of an irreversible antimuscarinic agent for purposes which may include prevention, amelioration, or cure of the disease or its symptoms.

The present invention is based on three primary approaches to the treatment of incontinence and other bladder diseases. Each approach avoids some of the difficulties with which this field is currently plagued.

A first approach employs the quaternary form of any antimuscarinic agent having a long duration of action. To carry out this approach, one may quaternize any known antimuscarinic compound by chemical modification of the nonquaternary nitrogen (typically a tertiary amine group) with a group as is disclosed herein. Alternatively, the quaternary compound may be created using an appropriate synthetic scheme to synthesize the agent already in quaternary form. All the synthetic schemes and methods intended herein are well-known to those skilled in the art of organic synthesis and medicinal chemistry and can be ascertained for a given compound without undue experimentation. One such reaction is the Michael addition.

A prototypical agent of this first quaternary class of compounds is methyl quinuclidinyl benzilate (FIG. 1B; abbreviated herein "MeQNB"), a retired product from Hoffman-LaRoche (generic name: clidinium; trade name: Quarzan®). Clidinium is also a component of Librax® (in combination with chlordiazepoxide), which is used to treat irritable bowel syndrome. MeQNB is a quaternary form of QNB in which the heterocycle nitrogen is substituted with the methyl group. Radiolabeled [$^3$H] QNB is a standard ligand used in muscarinic receptor binding assays to evaluate other compounds. While MeQNB may be appropriate for use in human clinical trials for proof of concept, other quinuclidine derivatives described herein are expected to have longer durations of action. It appears that may such quaternary compound have not been synthesized by others (Beilstein/Chemical Abstracts search). Strategies for the synthesis of the nonquaternary anticholinergic compounds that the present invention employs in this quaternary form were published by L. Abood long ago, as is discussed below. The present application is directed to the use of any such quaternary compounds for treating urinary incontinence.

The second approach is the use of muscarinic antagonists, preferably quaternary, that are modified to include a reactive group such as a mustard group, another alkylating moiety, or any other group that confers upon the compound prolonged and substantially irreversible action. A prototypical agent of this class is 4-DAMP bromo mustard, an irreversible and selective $M_3$ antagonist, shown in FIG. 1N (when Z is Br). The duration of action of 4-DAMP bromo mustard in vivo, let alone in the bladder, has not been well characterized. Because of the effect of the mustard group, even muscarinic agonists can be useful for the present invention and in fact converted into effective blockers. Some such substantially irreversible cholinergic agonists have been studied in rats. After an initial brief agonist effect, the agent BM130, an oxotremorine mustard, reduced sensitivity to cholinergic agonists. This compound was effective for about three weeks on some endpoints in laboratory animals. The production of new receptors is not necessarily the factor limiting the duration of action of agents of this class; studies indicate that the receptors are regenerated as these compounds degenerate in situ.

The third approach of the present invention is the use of substantially irreversible agents affecting second messenger systems. Anhydroecgonine esters (AEEs) are such agents, the prototype being AEME (see FIG. 1J). These agents do not appear to act as traditional muscarinic antagonists, but nevertheless reduce the efficacy of ACh in isolated bladder strip preparations. Preliminary evidence obtained by the present inventor suggests that these compounds act post-receptor but before signal transduction, presumably on second messenger systems (the G-protein cascade). These agents are described in U.S. Pat. No. 5,552,407 (by the present inventor and his and colleagues) and co-pending application U.S. Ser. No. 08/706,105 (by the present inventor) as irreversible antimuscarinic pharmaceutical compositions, either in the AEE family or quaternary atropine derivatives. These patent documents also describe use of such agents in preventing or inhibiting of muscarinic cholinergic responses in cells or tissues.

Treatment Methods

The new methods disclosed herein for treating bladder disease, in particular urinary incontinence, are characterized by intravesical administration of compounds most of which bind to muscarinic $M_3$ receptors in the bladder in a substantially irreversible manner, producing prolonged pharmacologic responses that overcome or prevent incontinence. Such compounds include the novel quaternary derivative compounds of this invention as well as other compounds which have the following properties:

(1) selective binding to muscarinic receptors (compared to non-muscarinic receptors), particular of the $M_3$ receptor subtype (compared to muscarinic receptors of the other subtypes) which predominate in the bladder.

(2) possess a quaternary nitrogen (generally a heterocyclic ring nitrogen) which renders the binding of the compound markedly less reversible than the binding of conventional (non-quaternary) anti-muscarinic agents. This has the effect of significantly reducing the frequency of treatment needed to achieve the same clinical effect.

Routes of Administration

A primary advantage of intravesical instillation is minimization of systemic side effects as discussed herein. A further advantage of the quaternary agents is that access to other tissues is prevented due to the poor absorption of these compounds. Thus, the combination of local application and lower absorption are the basis for the unexpected advantages of the present invention. This allows the achievement of higher doses of agents which would otherwise be intolerable or dangerous if given by other routes.

When the compositions are administered intravesically, they need not possess as a high degree of selectivity for the $M_3$ receptor subtype as compound given systemically. Thus, when using this route, less selective muscarinic antagonists can be used successfully (compared to systemic administration).

Because this route of administration provides the drug locally or regionally, and absorption into the circulation is less of a concern, it is not absolutely necessary that the agents have a quaternary nitrogen to prevent systemic absorption or entry into the CNS. Similarly, when using this route, lipophilicity of the composition does not have to be as great or the side chains as bulky to obtain the desired prolonged action on bladder function.

I. Quinuclidine Derivatives

Figure 1A:
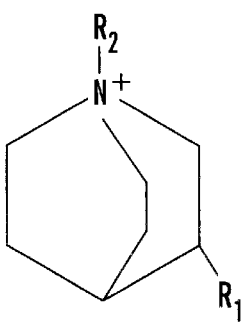
FIGS. 1A–N show the chemical structures of derivatives of several classes of antimuscarinic agents that comprise the compositions and are useful in the methods of the present invention. The name is given below the structure.
Figure 1B:
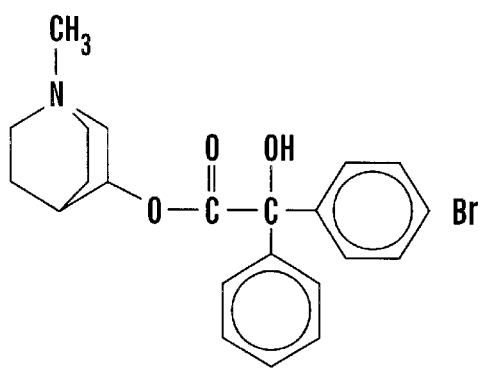
Figure 1C:
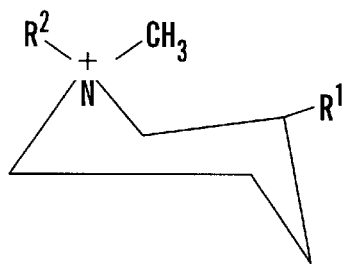

Quinuclidinyl benzilate (QNB) is a compound of FIG. 1A, wherein the ring nitrogen is in tertiary (i.e., no $R^2$ substituent) rather than quaternary form, and $R^1$ is:

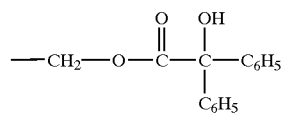

The quaternary compound, methyl QNB or MeQNB, wherein $R^2$ is $CH_3$, is approved for use in humans in salt form as "clinidium bromide." This compound may have a more prolonged duration of action than oxybutynin (Ditropan®). Hoffman LaRoche's patent for esters of azabicycloalkane alcohols and their salts, including quinuclidinol, QNB and MeQNB (U.S. Pat. No. 2,648,667) expired in 1970. Orally, MeQNB has a spectrum of side-effects and contraindications comparable to oxybutynin. However, in accordance with this invention, MeQNB and other quaternary quinuclidine analogues should be free of anticholinergic side effects when administered intravesically as disclosed herein.

The FDA approved oral dosage for MeQNB is up to 5 mg, four times per day (for a total of 20 mg/day). The FDA Summary Basis of Approval (SBA) includes a "Pharmacologist Review of NDA 10-355" of the submitted materials dated 14-JUN-74. This document described animal studies of clidinium bromide including acute dosing by oral and parenteral routes, chronic oral dosing of one year duration in dogs and rats at levels up to 50 and 100 times the daily human dose, as well as the usual gamut of reproductive and drug metabolism studies, all of which obviously supported the drug's safety. Accordingly, no objection was raised to the marketing of this anticholinergic agent as an antispasmodic in adjunctive treatment of peptic ulcers. No preclinical animal studies aroused concern as to the use of clidinium bromide in humans.

Other Derivatives of Quinuclidine and of QNB

Information derived from studies by the U.S. military of "belladonoid" agents (agents with actions similar to atropine which was derived from Belladona plants) led to the present inventor's conception that certain long-acting derivatives of quinuclidine or QNB may be further modified, preferably by creating a quaternary ring nitrogen, for use in the treatment of bladder disease.

The class of compounds of which QNB is a member are 1-glycolate esters of heterocyclic amino alcohols (1-azabicycloalkanols) having the general formula:

$$R_1-Y-Z-\overset{O}{\overset{\|}{C}}-\overset{R_2}{\underset{R_4}{\overset{|}{C}}}-R_3$$

$R_2$ is typically an —OH group (i.e., the compounds are alcohols). Again, for QNB, $R_1$ in FIG. 1M is quinuclidinyl ($C_7H_{13}N$) (see FIG. 1A and FIG. 1B), Y is a chemical bound, Z is O, $R_2$ is OH, and $R_3$ and $R_4$ are phenyl ($C_6H_5$) groups, as shown below.

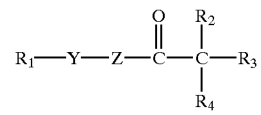

However, substitution of a cyclopentyl group for one phenyl group so that $R_4$ is now $C_5H_9$, results in a compound with markedly prolonged duration of action as described below.

A compound designated 3167 or EA 3167 by the Army was tested in humans, and is described in the proceedings of a conference held at Aberdeen Proving Grounds, Md., in July 1986 ("Workshop on the Feasibility of Using Incapacitation Agents Against Terrorists"). Compound 3167 was noted to be the longest acting compound in the series of belladonoids reviewed. It was tested in prison inmates at what were thought to be threshold doses and, just as the supposed threshold was approached, one individual developed a full-blown psychotic response and required daily physostigmine for two weeks to return to normalcy. It was concluded that compound 3167 had a duration of action of up to three weeks. Inquiries by the present inventor revealed compound 3167 to be 3-quinuclidinyl cyclopentylphenylglycolate, which is FIG. 1A wherein $R^1$ is

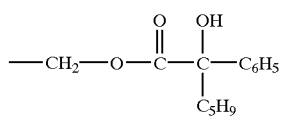

(This can also be characterized as the compound of FIG. 1M, wherein $R_1$ is 3-quinuclidinyl, Y is $CH_2$, Z is O, $R_2$ is OH, $R_3$ and $R_4$ are phenyl).

Thus, this compound differs from QNB only in that one phenyl group is replaced with a cyclopentyl group. Based on the properties described above, this compound and its quaternized derivative (e.g., N-methyl) are strong candidates as drugs for treating bladder disease as intended herein.

Figure 1D:
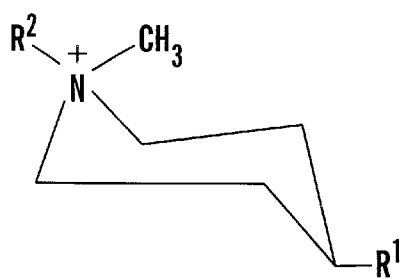
Figure 1E:
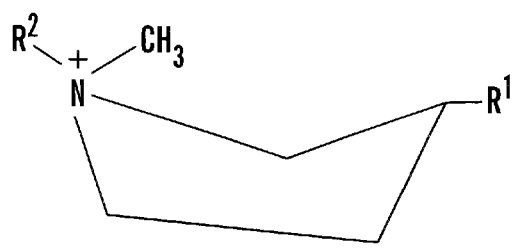
Figure 1F:
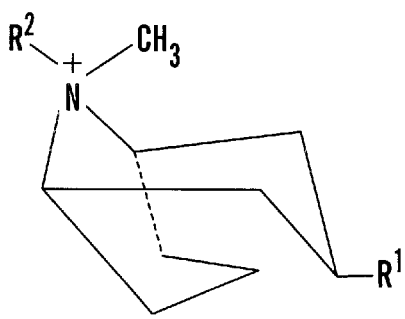
Figure 1G:
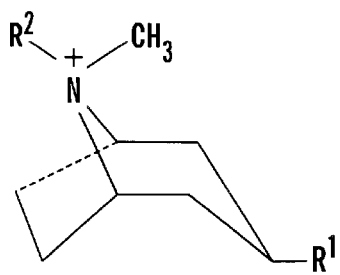

The present inventor learned that the structures of two other compounds given code numbers EA 3580 and EA 3443 by the U.S. Army were, respectively, N-methyl-4-piperidyl cyclobutylphenylglycolate and N-methyl-4-piperidyl cyclopentyl-phenylglycolate, both of which are included in FIG. 1D. These compounds are also useful for this invention. The nonquaternary compound 3167 has a relative binding index (to tissues) of 155 in comparison with QNB, consistent with a prolonged duration of action (Rzeszotarski et al. 1982, supra).

A number of the compound families of the present invention came to the inventor's attention from discussions with the late Dr. Leo Abood of the University of Rochester who had been studying anticholinergic compounds having CNS activity (psychotomimetics, etc.) both in an academic and defense context. This work is reviewed in the following two documents which are hereby incorporated by reference in their entirety:

(1) L. G. Abood, *The Psychotomimetic Glycolate Esters,* Chapter 4, In: *Drugs Affecting the Central Nervous System,* Vol. 2 (A. Burger, ed.), 1968, Dekker, Inc., New York, pp. 127–167.

(b) L. G. Abood, *Anticholinergics, Chapter 15, in: Psychotropic Agents, Part III: Alcohol and Psychotomimetics, Psychotropic Effects of Central Acting Drugs,* (F. Hoffmeister et al., ed.), Springer-Verlag, Berlin, 1982, pp. 331–347.

The compounds disclosed in the foregoing documents that are particularly applicable to the present invention (either as described or after the modifications taught herein) are the family of glycolate esters of heterocyclic amino alcohols having the general formula below (in FIG. 1M)

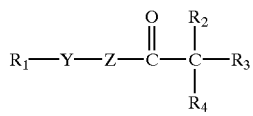

In preferred embodiments of the present invention, the radicals and substituents in FIG. 1M are as follows:

$R_1$ is a heterocyclic N-substituted ring, preferably piperidinyl, pyrrolidinyl, quinuclidinyl, granatanyl, or tropinyl, and the nitrogen is most preferably quaternary;

Y is a chemical bond or a lower alkyl group;

Z is O or S;

$R_2$ is OH, Cl, or an acyl alcohol or chloride; and $R_3$ and $R_4$ are any combination of a substituted or unsubstituted phenyl, a substituted or unsubstituted cycloalkyl, a straight or branched chain alkyl, alkenyl or alkynyl.

Activities of a number of these compounds have been evaluated either in behavioral or cholinergic pharmacological test, thus reflecting both general anticholinergic as well as CNS-specific activities. Pure peripheral antimuscarinic activity was assessed by testing contraction of ileal strips. The following generalizations may be made regarding the anticholinergic (and, where known, its relationship to the psychotomimetic) potency of these compounds.

General Point on Stereospecificity

Compounds of FIG. 1M, substituted as above, include scopolamine and related natural alkaloids and may exist as optical isomers due to the asymmetric C of both the amino alcohol and the acid moiety. Of the two enantiomers of 3-diphenylacetyl quinuclidine, the (−)-isomer has 25 times the antispasmodic potency of the (+)-isomer. The antispasmodic potency of the two isomers of the quaternary derivative of 3-QNB were similar (Sternbach et al., supra).

Relation Between Pharmacological Potency and Receptor Affinity $K_i$ values (inhibition constant), which reflect receptor binding affinity of a series of 14 glycolate ester anticholinergic agents to their pharmacologic potency has been described (Baumgold, et al., *Brain Res.* 124:331–340 (1977)). Excellent correlation between pharmacologic potencies (behavioral) and certain physical constants was found for the quinuclidinol and piperidinol esters, but not for those having other heterocyclic amino rings such as tropinol and granatanol esters (Baumgold et al., *Life Sci.* 17:603–612 (1975). On the other hand, excellent correlation independent of the type of heterocyclic amino ring was observed between affinity constants and the ability of these anticholinergics to block the ACh-induced ileal contraction (Baumgold et al., 1977, supra). The (−)-isomer of 3-QNB had about 50 times the affinity of the (+)-isomer for a synaptic brain membrane preparation. The relative binding affinities of the two isomers was still less than the 200:1 potency ratio found in behavioral tests.

Conformational Analysis of Glycolate Esters

The effects of these esters depends upon the charge and availability of the lone electron pair of the ring N. Before the structure of muscarinic receptors was available for modeling, it was assumed that the primary site of drug attachment is an electrophilic center of the receptor molecule. The accessibility of this center is influenced by steric factors affecting the nonbonded electron pair of the heterocyclic N atom. Now, as knowledge of the receptor structure has increased. See, for example, Goldstein, A. et al., *Principles of Drug Action: The Basis of Pharmacology,* 2nd ed., John Wiley and Sons, New York, N.Y., 1992, pages 22–32; R. K. Gordon et al., *Molec. Pharm.* 36:66–772 (1989); G. Nordvall et al., *J. Med. Chem.* 36:967–976 (1993), which references are incorporated by reference in their entirety. See FIG. 2, herein, which is a representation of the ligand binding site of a muscarinic receptor shown enveloping an antagonist molecule (taken from Gordon et al, supra, FIG. 5).

Stereochemical considerations may also account for the diminution of pharmacological activity resulting from alkyl substitution of the carbons adjacent to the ring N, and the diminished potency with increasing chain length of the N-alkyl substituent. The nucleophilicity of the heterocyclic N appears to be an essential requirement for pharmacological activity, but steric-configurational factors optimizing drug-receptor interactions are also important. Thermodynamic studies of muscarinic receptor (in brain) suggest that hydrophobic forces are preponderant over ionic and polar forces. Chaotropic ions which weaken hydrophobic interactions by disrupting water structure, reversibly decrease the affinity of anticholinergic agents to receptors.

Figure 2:
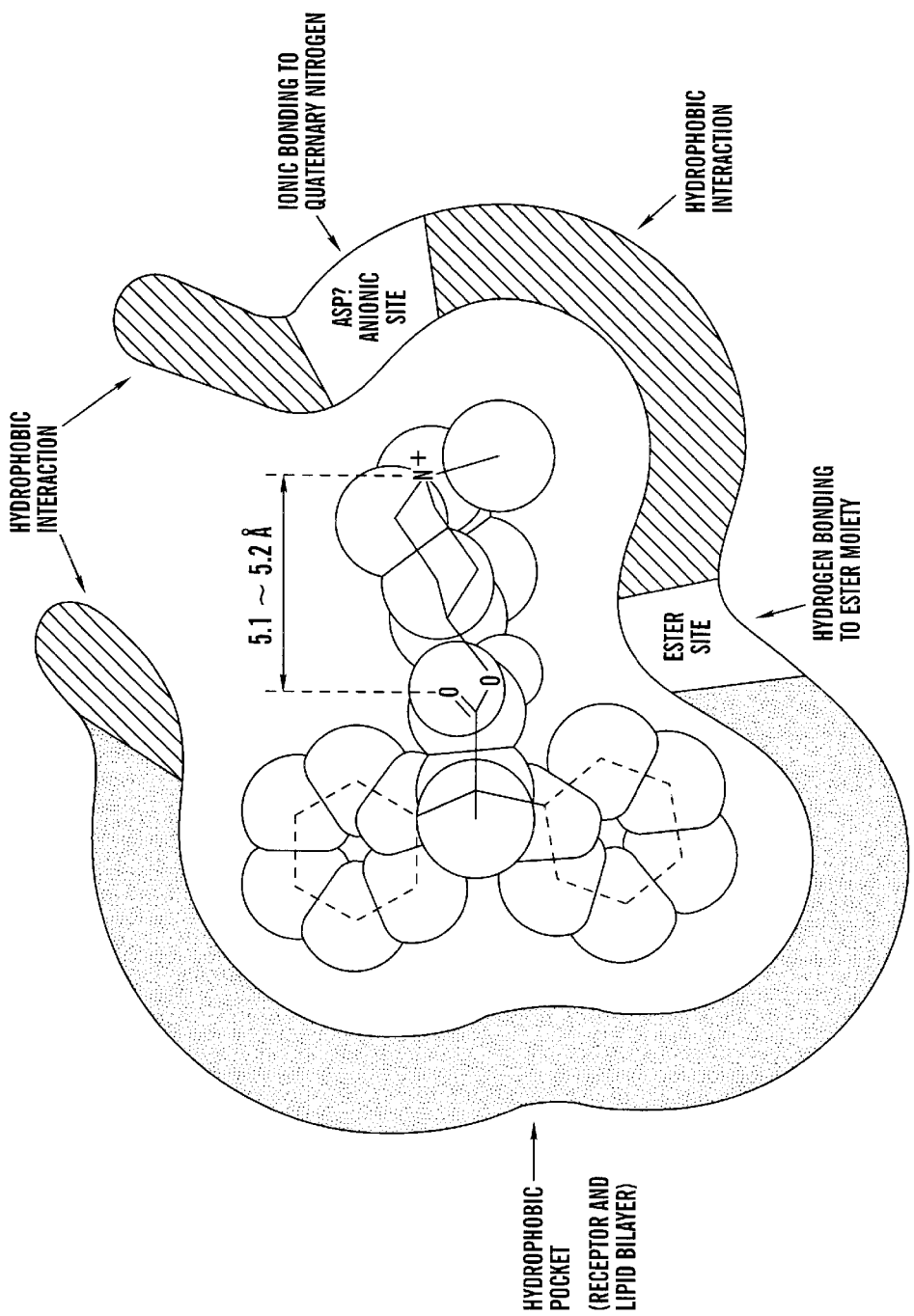
FIG. 2 is a representation of a model of the binding of a muscarinic ligand (antagonist) to a muscarinic receptor. The antagonist shown is N-methyl-4-piperidyl 2,2-diphenylpropionate. This structure is shown in FIG. 1D where $R^2$ is absent (i.e., the compound is a tertiary amine) and $R^1$ is.

The structure shown in FIG. 2 is used herein as a basis for testing various candidate agents for use in accordance with this invention. Thus, in addition to the conventional screening assays based on binding or pharmacological activity, a three dimensional molecular diagram of a compound under consideration for utility according to this invention is drawn as is the antagonist in FIG. 2. The planarity, length and size of the substituent groups is evaluated in light of this receptor configuration. Similarly, any other known or later devised structural model of the muscarinic receptor, preferably of the $M_3$ subtype, may be employed just as the model in FIG. 2 for examining the fit of a compound under analysis. Improved fit to the receptor correlates with activity in treating bladder disease. It is noteworthy that, based on the knowledge of the receptor, muscarinic blockers of the present invention should have a bond distance of about 5.0–5.2 Å between the heterocyclic, preferably quaternary, nitrogen atom and the carbonyl oxygen or ester bond. This is also shown in Goldstein et al., supra, at page 26, where, for the natural agonist ACh, the distance between the quaternary nitrogen and the carbonyl carbon is 5 Å. The key structural elements for proper engagement of the muscarinic receptor are the positively charged N that interacts with an anionic site in the receptor (possibly associated with Asp residue 105) and a carbonyl or similar group that reacts with a carbonyl binding site (Goldstein et al., at page 32) or "ester site" (FIG. 2). The hydrophobic pocket of the receptor accommodates two nonpolar groups, such as two phenyl groups, or a phenyl and a cycloalkyl, etc. As indicated in Nordvall et al., supra, the agonist binding site of the $M_1$ receptor subtype is fully defined by the following nine amino acid residues Asp105, Leu156, Thr192, Ala193, Ala196, Trp378, Tyr381, Asn382, and Val385.

As disclosed in more detail below, Peterson, J. S. et al., *J. Auton. Pharmac.* 10:65–73 (1990) describes what is known in the art about the potency and rank order of activity of various muscarinic antagonists on carbachol-induced contractions of bladder tissue strips in vitro and the relation of these measurements to pharmacologic effects on the bladder in vivo.

Quinuclidinyl Esters (1) Among the most potent glycolate esters are those of 3-quinuclidinol which are comparable in efficacy to the 4-piperidyl esters (discussed below). A methyl substitution in the 2 (cis) of the quinuclidine ring diminishes potency. QNB is an extremely potent (psychotomimetic) agent of this series. A unique feature of QNB is its extreme rigidity which imposes severe restrictions on the rotational and translational movements of the C and N atoms. This rigidity imposes restrictions on the 3-acyl substituent so that it is incapable of intramolecular hydrogen bonding, chelation, electronic interactions with the N, interactions which would diminish drug efficacy.

Piperidyl and Pyrrolidyl Esters

The formulas of these compounds are shown (in their quaternary form) in FIGS. 1C–1E (N-methyl-3-piperidinyl, N-methyl-4-piperidinyl and N-methyl-3-pyrrolidyl, respectively). The relevant properties of these compounds are set forth below. This analysis is based on the $R^1$ group being:

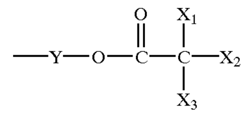

(1) Although $X_2$ should be a lower alkyl for maximal CNS action, this is not the case for general anticholinergic potency. Thus, $X_2$ may be higher alkyl, alkenyl, amino or aminoalkyl. Quaternization of the nitrogen abolishes CNS but not anticholinergic activity. This is an important property for the present invention to minimize side effects. Thus, quaternized piperidyl and pyrrolidyl esters of FIGS. 1C–1E are preferred in the present invention.

(2) $X_1$ is preferably H, or more preferably OH for maximal anticholinergic activity. A second or lone OH group in the β position of a cycloalkyl group in the acid moiety diminishes anticholinergic potency.

(3) $X_2$ and $X_3$ may be straight or branched chain C1–C10 alkyl, alkenyl or alkynyl, C3–C7 cycloalkyl, aryl, or araalkyl. Preferable combinations for $X_2$ and $X_3$ are, cycloalkyl+phenyl, phenyl+phenyl, phenyl+unsaturated alkyl (straight or branched), cycloalkyl+unsaturated alkyl and phenyl+alkyl. It is preferred to increase the length of the alkyl chain in $X_3$ when $X_2$ is phenyl or cycloalkyl. For maximal duration of action, it is preferred that number of C atoms in the cycloalkyl ring be 5.

(4) Substitution of the pyrrolidyl and piperidyl esters in ring position 3 (FIG. 1C) or 4 (FIG. 1D) results in comparable anticholinergic potency. With both piperidine and pyrrolidine ring types, potency is maximal when Y above is a chemical bond. To decrease undesired CNS activity, Y is a branched alkyl group with increasing chain length from C5–10. Substitution of groups such as halides, alkyl, alkoxy, or phenyl in one or both phenyl rings of the acid moiety diminishes anticholinergic potency.

(6) In the piperidyl series, rank order of potency with respect to the ester position on the ring was: 4-position>3-position>2-position.

(7) The thioesters of pyrrolidine and piperidine had reduced anticholinergic activity compared to esters; however, the same structure-activity relations exist. The duration of action of the thioesters is presumably less than that of the esters because of the greater ease of hydrolysis of this bond.

Esters of Other Heterocyclic Aminoalcohols

In general, the tropinyl (FIG. 1G) , granatanyl (FIG. 1F) and quinuclidinyl (FIG. 1A) esters are comparable in general anticholinergic potency (although esters of 3-tropinol and 3-granatanol, less active psychotomimetically than are the 3-quinuclidinyl or 4-piperidyl esters, are comparable in activity to the corresponding 3-piperidyl esters).

The information on peripheral anticholinergic activity described above is based primarily on studies of smooth muscle including ileum, uterus, iris, sphincter and blood vessels as well as nerves innervating these structures, such as the oculomotor, ciliary, vagus and other branches of the parasympathetic nervous system. It is known that the glycolate esters exert their spasmolytic action by a variety of mechanisms, primarily acting on muscle.

Glycolate esters have been observed to have various autonomic actions in humans. The autonomic (peripheral) effects include mydriasis, dryness of mouth, hyperemia and erythema, tachycardia, hypertension, and spasmolysis. A number of studies were performed with Ditran® (a mixture of about 70% pyrrolidyl ester and about 30% piperidyl ester). However, similar effects were observed following treatment with quinuclidinyl, tropanyl and granatanyl esters. It was believed that the esters acted in part by restricting the availability of ACh at cholinergic neurons by preventing release. This conforms with the "stabilizing" action of the glycolate esters on biological membranes.

Physical Properties of the Glycolates=N-methyl-3-pyrrolidyl methyl cyclopentylphenylglycolate (PMCG)

For purposes of exemplification relevant to the other molecules of this general class, the properties of PMCG will be discussed. Examination of PMCG reveals two distinct moieties: a hydrophilic cationic ring nitrogen and a glycolic acid containing a highly lipophilic phenyl and cyclopentyl group.

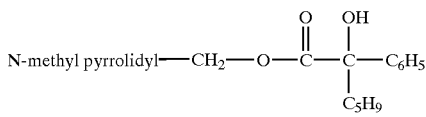

The cationic nitrogen can form electrostatic bonds with acidic groups of proteins, polysaccharides and nucleic acids. These compounds can form salts with a variety of naturally occurring inorganic and organic acids.

Among the important factors determining the action of a drug on the CNS were the lipophilic characteristics of the undissociated molecule and the degree of ionization. Higher lipid solubility and lipophilicity are considered to be advantageous for activity in the bladder in accordance with this invention.

Hydrogen Bonding and Anticholinergic Action

The presence of the OH group in the glycolic acid residue contributes to the formation of both intermolecular and intramolecular hydrogen bonds. Anticholinergic action was believed to be diminished by intramolecular hydrogen bonding between the carbonyl O and the OH group. However, such bonding would not be expected to be extensive because of the long hydrogen-oxygen distance and the unfavorable orientation of the hydrogen atom with respect to the oxygen.

Acid Strength and Drug Potency

Another factor influencing anticholinergic potency is the acid strength of the acid moiety. Anticholinergic potency increases with increasing acid strength. This is exemplified in the following series of 3-piperidyl esters shown in order of increasing potency and acid strength: benzilate>diphenyl acetate>phenyl acetate>acetate. Replacement of the phenyl group in benzilic acid by an alkyl group greatly reduces pharmacological potency. The major contributory factor to the rate of acid hydrolysis of the glycolate esters following phenyl replacement or substitution would be steric. The significance of acid strength for pharmacological efficacy appears to be linked to the OH group which is known to be more important for CNS activity. Replacing OH with another electronegative substituent abolishes activity unless the group is capable of undergoing hydrolysis (e.g., halogen or acyl).

Coplanarity of the phenyl rings is a requirement for activity, a factor which contributes to stabilization of the carbonium ion.

Conformational Analysis of Glycolate Esters and Biological Activity a. Quinuclidinyl A consideration of structure activity relationships, pK, solubility and other physical characteristics leads to the conclusion that the pharmacological activity of the glycolate esters depends upon the charge and availability of the lone electron pair of the ring nitrogen. The most active agents of this series are the bicyclic bridged aminoalcohol 3-(±)-quinuclidinol and derivatives. Among the key stereochemical properties of this alcohol is its extreme rigidity which imposes severe restrictions on rotational and translational movements of the C and N atoms. Because of this rigidity, the acyl portion of the ester and the non-bonded electron pair of the amino group are directed oppositely, so that the intramolecular hydrogen bonding, chelation, and electronic interaction of the neighboring groups are less likely b. Piperidinyl N-methyl piperidine is expected to assume a configuration favoring an interaction such that the non-bonded electron pair is accessible. This molecule is most stable in chair form where the methyl substituent is either equatorial or axial. This similarity in nucleophilicity and pharmacological potency of the piperidinyl and quinuclidinyl esters appears plausible.

Added Reactive Groups and Chains

One general strategy of the present invention is the addition of reactive groups into the various antimuscarinic compounds to promote the irreversible binding of the compounds with the receptor or other cellular structures, leading to prolonged duration of action. Such groups are well-known in the art. Preferred groups include alkylating agents such as mustards. The reactive groups may be part of the compound used for treatment, or may be generated after the compound is administered, as is discussed below for aziridinium ions. Although the presence of these reactive groups is intended to confer covalent binding capacity on the ligand to which they are bonded so that the antagonist molecule can bind covalently to its receptor or to other nearby cellular structures, such a mode of action is not required. Rather if these groups render the ligand "functionally" substantially irreversible, if not chemically so, they are still behaving in accordance with this invention.

Examples of preferred reactive groups include an isothiocyanate, a thiocyanate, a fumaramate methyl ester, a carboxyl methyl ester, a p-azidophenylethylester, a p-isothiocyanatophenylethylester, a p(bromacetoamido)-phenylethylester and a 3-iodo-4-azidophenylethylester. Esterification of atropine with α-formylphenacetic acid results in the formation of an ester which is reduced to isopropylnoratropine, which can then be quaternized with methylbromide (Deckers, W., *Postgrad. Med. J.* 51(Suppl 7):76–81 (1975)). Other groups with desired properties are p-halo, p-methyl and p-nitrocinnamoylamino groups. These electron-withdrawing moieties in the para position make the cinnamoylamino function a better Michael acceptor. These chains have been shown to render opioid antagonists functionally irreversible (Sebastian, A. et al., *J. Med. Chem* 36:3154 (1993); Burke, T. F., *Symposium on the Pharmacology of Irreversible Opioid Antagonists,* The College of Problems of Drug Dependence, June 21, 1992, Keystone, Colo.; Comer, S. D. et al., *J. Pharm. Exper. Ther.* 262:1051 (1992)). It is not clear in every case whether the nonequilibrium behavior of these derivatives is due to true covalent binding to their respective receptors.

4-DAMP Mustards and Their Derivatives

Examples of known compounds that are useful in the methods of this invention are: N-(2-chloroethyl)-4-piperidinyl diphenylacetate, also known as 4-DAMP mustard; the related compound N-(3-chloropropyl)-4-piperidinyl diphenylacetate; N-(2-bromoethyl)-4-piperidinyl diphenylacetate, termed 4-DAMP bromo mustard (Griffin, M. T. et al., *J. Pharmacol. Exp. Ther.* 266:301–305, 1993).

The aziridinium ion of the 4-DAMP family of compounds is the active agent, and the ions are formed from the spontaneous cyclization of the parent. This occurs virtually instantaneously with 4-DAMP bromo mustard. Cyclization of the chloro mustard compound proceeds much more slowly. Consequently, after intravenous administration to a mammal, measurable irreversible inhibition of muscarinic receptor binding occurs in the central nervous system. This result does not occur with the bromo mustard compound unless a very high dose is administered (2.5 μmol/kg iv), a dose sufficient to alkylate more than 95% of the receptors in both the heart and submaxillary gland. High concentrations result in the non-selective alkylation of all muscarinic receptor subtypes. However, at lower concentrations in the order of 1–10 nM, the aziridinium ions selectively alkylate the $M_3$ receptor subtype. This is attributable to the 12.9-fold greater affinity of the aziridinium ion for the $M_3$ compared to the $M_2$ receptor subtype (demonstrated using recombinant muscarinic receptors in transfected Chinese hamster ovary (CHO) cells (Ehlert, F. J. et al., *J. Pharmaco Exp. Ther.* 276:405–410, 1996). Treatment in vivo with low doses of 4-DAMP mustard selectively inactivates $M_3$ receptors compared to $M_2$ receptors, although at higher doses, such selectivity is lost (Thomas, E. A. et al., *Proc West Pharmacol Soc.* 35:233–237 (1992).

Since the $M_3$ receptor subtype predominates in the bladder, use of agents with $M_3$ selectivity is preferred. However compounds with lower affinity or selectivity for this subtype of receptor (for example, $M_1$-selective antagonists) can still be effective herein because of (1) the direct instillation into the bladder resulting in a high local concentration of drug, (2) the prolonged duration of action characteristic of the compounds of this invention and (3) the limited absorption of these compounds from the bladder. Thus, agents with lower intrinsic potency and selectivity are still useful if they are preferentially excluded from crossing the bladder wall because this would permit the attainment of higher intravesical concentrations to achieve the desired result. Thus in the methods of the present invention, the class of useful therapeutic agents would not be limited to prototypical compounds like 4-DAMP bromo mustard or an $M_3$ receptor antagonist, but would include virtually any anticholinergic agent which has been modified as described herein, for example, by rendering the ring nitrogen quaternary, by the addition of a reactive moiety such as a mustard, by the inclusion of a bulky group, etc.

Irreversible anticholinergic agents of relatively high molecular weight may be useful for the present purposes and can attain the selective activity even if they are not quaternary compounds. Thus, in one embodiment, the molecular weight of known anticholinergic agents is increased by the addition of polymers or other bulky groups to inactive sites of the molecule that do not interfere sterically with the molecule's fundamental receptor-directed action.

The strategies that are the basis of the present invention, (a) quaternization, (b) increasing the molecular mass, or (c) addition of reactive moieties, can be applied to oxybutynin, its derivatives or to newer generation compounds developed to replace oxybutynin.

In a study directed toward development of agents possessing the beneficial properties of oxybutynin, but having a longer duration of action, Carter J P et al., *J Med Chem* 34:3065–3074 (1991) tested a series of metabolically more stable keto analogues of the parent ester, i.e., substituted 7-amino-1-hydroxy-5-heptyn-2-ones along with some analogues and derivatives. These compounds were evaluated for in vitro and in vivo antimuscarinic action in guinea pig preparations. Several members of the series were potent antimuscarinics having a longer duration of activity than that of oxybutynin in a guinea pig cystometrogram model. A preferred compound which has a 5-fold greater duration of action than oxybutynin, 1-cyclobutyl-7-(dimethylamino)-1-hydroxy-1-phenyl-5-heptyn-2-one (14b) maybe modified and used in accordance with this invention.

A series of N-substituted 5-(aminomethyl)-3,3-diphenyl-2(3H)-furanones, conformationally-constrained lactone relatives of benactyzine has been prepared Kaiser C et al., *J Med Chem.* 35:44154424 (1992) and tested in several paradigms that measure $M_1$, $M_2$, and $M_3$ receptor antagonist activity. Selected members of the series that displayed potency and/or selectivity in these tests were studied for their effects on urinary bladder contraction, mydriasis, and salivation in guinea pigs.

Incorporation of the amino functionality into an imidazole or pyrazole ring results in some novel, potent, and selective antimuscarinic agents. Appropriate alkyl substitution of position 2 of the imidazole strikingly affected muscarinic, particularly $M_3$, receptor activity and may reflect a complementary site of interaction. Some of the compounds selectively reduced bladder pressure in a cystometrogram model without producing concomitant mydriatic and salivary effects. These studies led to the identification of (R)-[(2-isopropyl-1H-imidazol-1-yl)methyl]-4,5-dihydro-3,3-diphenyl-2(3H)-furanone as a clinical candidate for treating urinary bladder dysfunction.

A new class of substituted 1-phenyl-3-piperazinyl-2-propanones with antimuscarinic activity was reported (Kaiser, C et al., *J Med Chem* 36:610–616 (1993) as part of a search for new antimuscarinic agents with potential utility in treating urinary incontinence associated with bladder muscle instability. Potency and selectivity was influenced most notably by the nature of the substituent group on the terminal nitrogen of the piperazine moiety. Benzyl substitution was particularly advantageous in producing compounds with functional $M_3$ receptor selectivity and bladder selectivity, thereby providing several candidates for clinical study. In vivo, 3-(4-benzyl-piperazinyl)-1-cyclobutyl-1-hydroxy-(1-phenyl-2-propanone demonstrated selective bladder function versus mydriatic and salivation responses. The corresponding 2-chlorobenzyl derivative (compound 25) is more than 178-fold selective for $M_3$ versus $M_1$ and $M_2$ receptors. 3-(4-benzylpiperazinyl)-1,1-diphenyl-1-hydroxy-2-propanone was 18-fold selective for $M_3$ versus $M_1$ and 242-fold selective for $M_3$ versus $M_2$ receptors, and, in guinea pigs, displayed 20- and 41-fold separations between bladder function and effect on mydriasis and salivation, respectively. Based on this, it appears that piperazinyl propanones interact with muscarinic receptors in a hydrogen-bonded form that presents a conformation similar to that apparently adopted by classical antimuscarinic agents.

Modified Atropine and its Active Derivatives

Figure 1H:
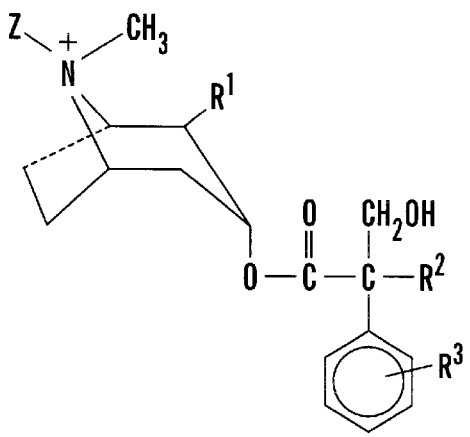
Figure 1I:
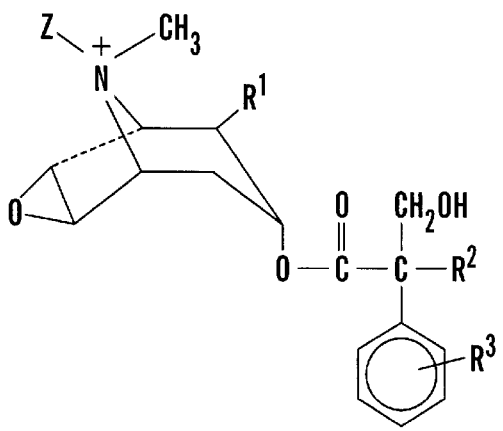

The structure of a generic quaternary derivative of atropine and atropine epoxide are shown in FIG. 1H and FIG. 1I, respectively. A list of preferred substituents at the four indicated positions in the structure include the following:

Anhydroecgonine Esters (AEE's) and Active Derivatives

Figure 1J:
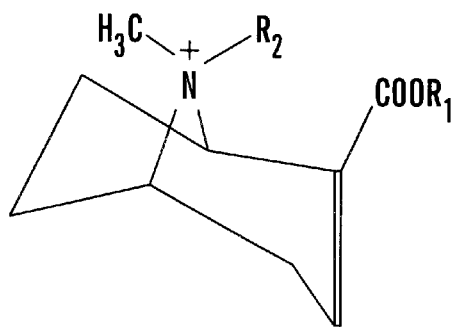
Figure 1K:
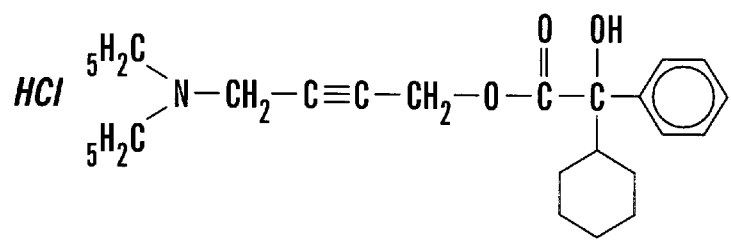
Figure 1L:
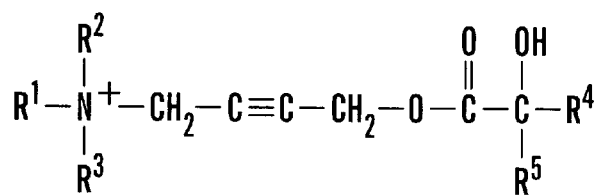
Figure 1M:
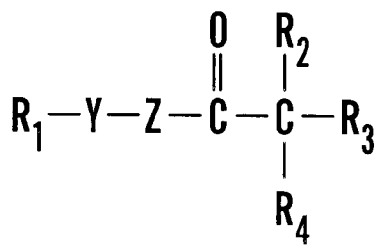
Figure 1N:
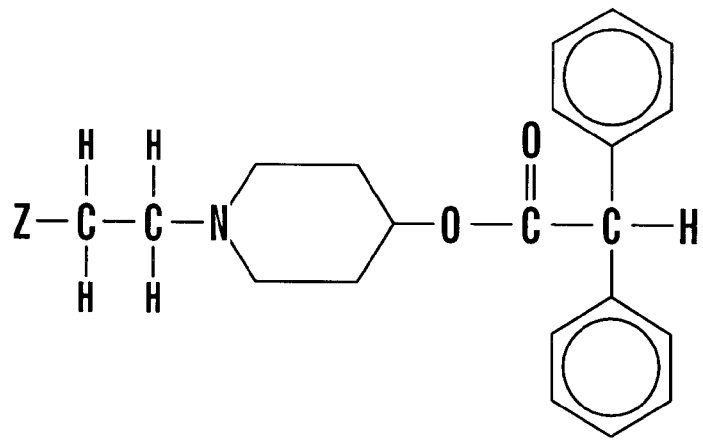

The compounds indicated by (FIG. 1J) are the preferred quaternary AEE's of this invention. Modifications of the tropane ring at any of two sites ($R_1$ or $R_2$; see below) in the molecule are included within the scope of the present invention. The structures described herein can be substituted in any one of these sites as indicated in FIG. 1J.

Below is a list of preferred substituents at the two indicated positions in the structure. The names of the compounds provided for the $R_1$-substituted compounds are based on the single noted substitution, where $R_2$ is a hydrogen atom. Preferred $R_1$ include $C_1$–$C_{10}$alkyl groups, which may be optionally aryl substituted. Preferably, the alkyl group or aryl substituted alkyl group is an active alkylating moiety or a group reactive with a cell surface component capable of forming a covalent bond. Preferred substitutions at $R_1$ are:

(1) $CH_3$ (anhydroecgonine methylester or AEME);
(2) $CH_2CH_3$ (anhydroecgonine ethyl ester);
(3) $(CH_2)_2CH_3$ (anhydroecgonine propylester);
(4) $(CH_2)_2C_6H_4$4-$N_3$ (anhydroecgonine-2β-carboxylic acid-2-(p-azidophenyl)ethylester;
(5) $(CH_2)_2C_6H_4$4-NCS (anhydroecgonine-2β-carboxylic acid-2-(p-isothiocyanatophenyl)ethylester;
(6) $(CH_2)_2C_6H_4$4-$NHCOCH_2Br$ (anhydroecgonine-2β-carboxylic acid-2-[p(bromacetoamido)phenyl] ethylester;
(7) $(CH_2)_2C_6H_3$3-I-4-$N_3$ (anhydroecgonine-2β-carboxylic acid-2-(3-iodo-4-azidophenyl)ethylester;

In the following four embodiments, the $COOR_1$ group is replaced with:

(8) $COCH_3$ (anhydroecgonine-2β-methyl ketone);
(9) $COCH_2CH_3$ (anhydroecgonine-2β-ethyl ketone);
(10) NCS (anhydroecgonine-2β-isothiocyanate); and
(11) SCN (anhydroecgonine-2β-thiocyanate).

$R_1$ substituents (1) to (3) above are AEME or alkylester variants of AEME. Substituents (4)–(7) are modeled on potential irreversible ligands for the dopamine transporter described by Carroll et al., *J. Med. Chem.* 35:1813–1817 (1992). Substituents (8) and (9) are 2β-alkylketone variants of AEME (*Eur. J. Pharmacol.* 244:93–97 (1993)). Substituents (10) and (11) are mustards.

Preferred AEME analogues or derivatives are those in which the carboxymethyl ester moiety of AEME is replaced by a substituent group which is an alkylating moiety or other reactive group which will form a covalent bond with the muscarinic receptor after ligand-receptor interaction. Preferred reactive groups are electron-withdrawing groups, including halide substituted aryl groups, and the like. By covalently bonding to the cell surface, presumably to the muscarinic (or other) receptor, such a derivative will have a relatively irreversible antimuscarinic mode of action. Of the compounds listed above, substituents (4)–(7), (10) and (11) have such properties.

β-funaltrexamine (β-FNA), the fumaramate methyl ester of naltrexamine is a narcotic antagonist having an alkylating moiety through which the compound binds irreversibly to the membrane after the ligand-receptor interaction. This agent does not provoke up-regulation of the number of receptors, as occurs with other narcotic antagonists. On the basis of these properties, a fumaramate methyl ester analogue of AEME is a useful antimuscarinic agent in accordance with the present invention. Another example is acetylethylcholine mustard, which is a cholinergic agonist that irreversibly binds to the muscarinic receptor.

Preferred substituents at the $R_2$ position (where the names are directed to compounds in which $R_1$ is methyl) include:

(1) H (anhydroecgonine methylester, AEME);
(2) $CH_3$ (N-methyl anhydroecgonine methylester);
(3) $CH_2CH_3$ (N-ethyl anhydroecgonine methylester);
(4) $CH(CH_3)_2$ (N-isopropyl anhydroecgonine methylester);
(5) $CH_2CH_2CH_3$ (N-propyl anhydroecgonine methylester);
(6) $CH_2CH_2CH_2CH_3$ (N-butyl anhydroecgonine methylester);
(7) $CH_3(CH)CH_2CH_3$ (N-sec-butyl anhydroecgonine methylester);
(8) $C(CH_3)_3$ (N tert-butyl anhydroecgonine methylester); and
(9) an amidine such as guanidine, formamidine or acetamidine.

Alkyl substituents at the bridge nitrogen result in the formation of quaternary compounds with limited solubility in lipid and reduced access to the central nervous system. Absorption from the bladder into the bloodstream is less likely for isopropyl or larger compounds. By varying the substituents, one of ordinary skill in the art may alter the pharmacokinetic profile and produce more selective effects. Replacing the "cationic head" of AEME and derivatives thereof with an amidine basic center may be useful for altering both the pharmacokinetics and pharmacodynamics of the compound (Cereda et al., *J. Med. Chem.* 33:2108–2113 (1990)). This may influence relative potency and selectivity at muscarinic receptors, which is important when the compound spreads systemically.

The stereochemistry of the $R_2$ substituents is expected to alter the pharmacologic potency of the compound. When oriented over the pyrrolidine ring, lesser potency is expected than when the substituent is oriented over the piperidine ring., i.e., endo to the three atom bridge of the tricyclic tropinyl skeleton. Synthesis of the compound having the endo configuration can be performed according to Deckers, W., supra. For example, a Robinson-Schopf condensation of succinic dialdehyde, isopropylamine and acetonedicarboxylic acid produces isopropylnortropinone which can be hydrogenated catalytically to isopropylnortropine.

A most preferred AEME analogue modification involves substituting at the nitrogen in the $R_2$ position an isopropyl group resulting in a quaternary amine which would enhance the potency and/or duration of action of the agent.

An additional substitution involves replacement of the C—C bond between $C_6$ and $C_7$ in the pyrrolidine ring portion of the tropine structure with an epoxide structure.

The irreversible effects of AEME are believed to be attributable to the interaction between this molecule and a receptor to which it binds. This may take the form of a Michael reaction in which the double bond opens and a new bond forms in its proximity. If this is the case, any of a number of electron-withdrawing substituents can be located in the $R_1$ position (see above), as long as the α-β unsaturated nature of the parent compound remains undisturbed. If the irreversibility is a property of the $R_1$ moiety itself rather than its effect of withdrawing an electron from the piperidine ring, then more reactive substituents in that position on AEME or on atropine would be preferred.

Testing Compound for Antimuscarinic Reactivity and Specificity.

The compounds are examined for muscarinic receptor subtype selectivity in binding assays with cell lines that have been transfected with the appropriate receptor gene, or with isolated cells or tissues that express the relevant receptor subtype(s). Known in vivo assays in guinea pigs measure effects on urinary bladder contraction, mydriasis, and salivation. A conventional $M_1$ receptor assay utilizes rat superior cervical ganglion (Newberry, N. R. et al., *Brit. J. Pharmacol.* 92:819–826 (1987); Roberts et al., *Eur. J. Pharmacol.* 186:257–265 (1990)). A conventional assay for $M_2$ activity uses electrically stimulated guinea pig atria tissue.

An $M_3$ assay uses guinea pig myenteric plexus (longitudinal muscle). Of course, assays for pharmacologic effects in vitro may be performed with the target tissue of this invention, bladder tissue (or detrusor muscle), and in vivo effects may be tested in intact animals. Assays have been described in guinea pigs and in miniature swine (minipigs) and yield highly correlated results (see below). Using any of these assays or models, it is possible to determine without undue experimentation whether a given compound has the requisite receptor binding activity, substantial irreversibility, prolonged pharmacologic activity and absence of undesired side effects to be useful for in the present invention.

Binding Assays for $M_3$ Muscarinic Receptors

As noted above, the $M_3$ muscarinic receptor is one of five known muscarinic cholinergic receptor subtypes (Bonner, T. I. et al., Science. 237:527–32, 1987; Neuron 1:403–410, 1988), all of which have been cloned. All five of these receptors bind non-selective cholinergic antagonists such as N-methylscopolamine (NMS) and QNB (Buckley et al., Mol. Pharm. 35:469–476, 1989). The $M_3$ receptor exhibits high affinity binding for the subtype-selective antagonist p-F-HHSiD (Ki=28 nM) and low affinity for methoctramine (Ki=408 nM) and pirenzepine (Ki=1497 nM) (Buckley et al, supra. This receptor is coupled to a signaling pathway involving phosphoinositol hydrolysis but not inhibition of cAMP levels (similarly to the $M_1$ receptor).

The assay may be performed using a transfected CHO-K1 cell line (Catalog # RB-HM3, 1998) is available commercially from Receptor Biology, Inc., Beltsville, Md. (The DNA has GenBank Accession Number: X15266). This material exhibits over 92% specific binding of [$^3$H]NMS at the $K_i$, and is suitable for routine binding and screening applications. For [$^3$H]NMS binding the $B_{max}$. is 1–2 pmol/mg protein and the $K_d$ is 0.01–0.1 nM. The receptor material is purchased as a frozen suspension of cell membranes, suspended in 10 mM Tris-HCl pH 7.2, 2 mM EDTA, 10% sucrose.

A preferred assay procedure is as follows: Thaw vials rapidly; dilute with binding buffer; homogenize. Keep on ice. Incubation buffer is phosphate buffered saline (PBS), pH 7.4. For binding, incubate 25 $\mu$g of membranes (100 $\mu$l of a 1:20 dilution) [$^3$H]N-methyl scopolamine (1.16 nM) and unlabelled test ligand in a total volume of 1 mL for 60 min at 25° C. Atropine, 0.5 $\mu$M, is used to define non-specific binding. Filter over Whatman 934-AH filters and wash filters 3x with ice-cold PBS. Under these conditions, approximately 2400 cpm of total binding can be obtained of which about 8% represents non-specific binding. For Scatchard analysis, use a total assay volume of 2 mL and increase the incubation time to 120 min at 25° C.

Similar receptor preparations for other muscarinic receptors are available from the same source, or may be prepared using routine skill by transfecting the available DNA into similar cell lines.

Quantitation of Muscarinic Receptors In Vivo

Quantitation of muscarinic receptors in vivo has been described (in myocardium of closed-chest dogs) using positron emission tomography (PET). Delforge, J. et al., Circulation 82:1494–1504 (1990). Similar techniques may be used in pigs. Animals are injected with trace amounts of [$^{11}$C]methyl QNB, a nonmetabolized receptor antagonist. This is followed 30 minutes later by injection of an excess of unlabeled methyl QNB (for displacement). Two additional injections of unlabeled methyl QNB with [$^{11}$C]methyl QNB (coinjection experiment) and without labeled methyl QNB (second displacement experiment) are administered after 70 and 120 minutes, respectively. This protocol allows evaluation of the quantity of available receptors ($B'_{max}$) as well as the association and dissociation constants ($k_{+1}$ and $k_{-1}$). In the Delforge study (supra), the average value of $B'_{max}$ was 42±11 pmols/ml tissue, the rate constants $k_{+1}$, $k_{-1}$ and $k_d$ were 0.6±0.1 ml·pmol$^{-1}$·min$^{-1}$, 0.27±0.03 ml·pmol$^-$ $_1$·min$^{-1}$, and 0.49±0.14 pmol$^{-1}$·ml$^{-1}$, respectively. Association of the antagonist is very rapid and dissociation is far from negligible. The dissociated ligand, however, has a high probability of a re-binding to a free receptor site instead of escaping into the microcirculation.

PET images obtained after injecting a trace amount of labeled methyl QNB are more representative of blood flow than of receptor density or affinity. They also suggested a simplified protocol consisting of a tracer injection of [$^{11}$C] methyl QNB and a second injection of excess cold methyl QNB which is sufficient to measure $B'_{max}$ and $K_d$ values in humans.

This protocol has been optimized for human studies (Delforge, J. et al., J. Nucl. Med. 34:981–991 (1993)) The protocol may include three injections: a tracer injection, followed 30 min later by injection of an excess of unlabeled methyl QNB (displacement) and then 30 min later by a simultaneous injection of unlabeled and labeled methyl QNB (coinjection). This protocol enables a separate evaluation of all parameters of a ligand-receptor model which includes three compartments and seven parameters. The complexity of this protocol appears inconvenient for clinical use. A simplified two-injection protocol (tracer injection and co-injection) may also be used (Delforge et al., supra). When these two protocols were compared in normal subjects (testing the myocardium), in regions of interest over the left ventricle, the mean value of the receptor concentration, $B'_{max}$, and the equilibrium dissociation constant $k_d$ were 26±7 pmol/ml tissue and 2.0±0.5 pmol/ml tissue, respectively. The possibility of nonspecific binding is accounted for by running a double-displacement protocol. The corresponding rate constant was found to be very low, 0.03 min$^{-1}$.

Deduction of receptor concentration, is achieved with a mathematical model that describes ligand-receptor interactions, the parameters (including receptor concentration) of which must be identified from the kinetic curves in a dynamic PET experiment. For example, it is now possible to quantify myocardial muscarinic receptors in the human heart noninvasively using PET with a simplified protocol by starting with a tracer injection of [$^{11}$C]methyl QNB followed 30 min later by co-injection of labeled and unlabeled methyl QNB. Because these protocols are completely noninvasive, it becomes feasible to investigate possible changes in receptor density and/or affinity in the bladder.

Animals Models of Bladder Function

Micturition is a complex reflex requiring an intact nervous system for the maintenance of continence. Agents which achieve systemic distribution may not display the same pattern of activity that might be predicted from in vitro assays of receptor affinity or smooth muscle function, since the agent of interest may act at multiple sites.

Guinea Pig Model

A guinea pig model is be used to perform a slow-filling cystometrogram that mimics the natural filling of the bladder; this technique is widely used in humans and animals to measure urodynamic parameters associated with bladder dysfunction. Successful therapeutic agents are expected to reduce peak intravesicular bladder pressure through an interaction with $M_3$ muscarinic receptors.

Guinea pigs are anesthetized with 15% (w/v) urethane solution (1.5 g/kg body weight i.p.). Urethane is the anesthetic of choice because it maintains the required spinal reflexes, including micturition. The anesthetized guinea pigs are placed supine on a heated pad and their bladders catheterized via the urethra with PE150 tubing. The urethral opening is tightly sutured to prevent leakage during the filling phase. The tubing is attached to a pressure transducer, a syringe pump for bladder filling, and an exit port to empty the bladder between trials.

The bladder is filled at a constant rate until a coordinated and sustained contraction occurs. The bladder is then drained, a five minute rest period ensues, and the cycle is repeated. Cumulative within-session dose-effect functions are determined by administering test agents either directly into the bladder, or by the usual parenteral routes (iv, sc, ip). Animals are be euthanized with 100 mg/kg sodium pentobarbital. Each animal is used as its own control. An ascending series of concentrations is tested in each animal in the rest period between each contraction and during the cystometry. Four animals are sufficient to establish confidence limits for each individual compound's dose-effect function.

Preparations of this type are the "first-tier" screen for compounds thought to have promise for the treatment of bladder disease. Alternative preparations include larger animals such as swine or non-human primates.

Swine Procedure

This will examine several potential medications in normal swine prepared for chronic measurement of bladder function, and in a model of urge incontinence produced by a single surgical intervention.

A minipig model is used to study normal patterns of micturition and to perform a slow-filling cystometrogram that mimics the natural filling of the bladder, as above.

Each pig is instrumented either with telemetry devices for the measurement of intraabdominal and intravesical pressure, or with catheters attached to subcutaneous ports for this purpose. Using either an indwelling transvesical catheter or with the insertion of a urethral catheter, the bladder is filled at a constant rate until a coordinated and sustained contraction associated with bladder emptying occurs. This cycle is repeat for several hours on each day of the experiment. On other days, normal patterns of micturition are observed, either with or without challenges with a diuretic or with supplemental hydration.

The duration of action of agents are described in tests with normal animals in which single doses are given on an experimental day, and effects noted on successive voids on that day or across days. Successful medications will have longer durations of action than agents currently used for the treatment of this disorder. Circumferential section of the bladder dome and immediate repair results in the delayed (2–3 weeks) production of a pattern of spontaneous bladder contraction resembling that observed in urge incontinence.

Reference drugs and test agents will be evaluated similarly in this animal model of urologic dysfunction. Animals will be euthanized with 100 mg/kg sodium pentobarbital i.v.

Swine (minipigs) are currently the species of choice for studies of bladder instability. Rats form urinary calculi in subacute preparations; even with antibiotic prevention, rats only produce approximately four sessions of data in the best studies to date. Unlike rats but like man, in the minipig the majority of parasympathetic ganglia lie in the detrusor muscle. Pigs display detrusor instability with bladder outlet obstruction, and display similar renal and bladder morphology, cystometry and cystoscopy. The majority of the parasympathetic excitatory innervation of the bladder is thought to enter from the pelvic plexus at the base of the bladder. Full-thickness bladder transection above the ureteric orifices should thus deprive the dome of the bladder of its motor innervation. This procedure is possible in pigs, as the blood flow to the dome passes through the superior pedicles and remains intact after transection. Circumferential transection and immediate repair of the bladder interrupts innervation within the organ resulting in spontaneous detrusor contractions approximately 20 days after surgery, while leaving remaining patterns of micturition intact.

Larger animals readily accommodate implantation of relatively large devices such as multiple subcutaneous ports and/or telemetry devices.

These tests evaluate efficacy and duration of action of the compositions of this invention in animal models of bladder function in normal bladders and in surgically-induced bladder dysfunction. Each animal is used as its own control. Four animals are sufficient to establish confidence limits for the dose-effect function of each reference compound. Oxybutynin (Ditropan®) is the standard agent used for incontinence pharmacotherapy. Isopropylatropine (ipratropium, Atrovent®) and methylatropine (Parmine®) have similar actions. The compounds of the invention must show comparable activity and have a prolonged duration of action. The duration of action of the reference compounds is hours; the test compounds are expected to have durations of action ranging from days to weeks.

General anesthesia (except urethane which is useful only in acute experiments) affects supraspinal afferents and impairs normal micturition reflexes. Thus it is necessary to study these processes in awake animals. The use of indwelling cannulae and telemetry devices as described herein are refinements of conventional techniques and minimizes the frequency of insertion of cannulae through the urethra for measurement of detrusor function.

Urodynamic studies using port-catheters. Awake animals are walked into a restraint stock or squeeze cage suitable for use with swine and ruminant species, and are restrained in an upright standing position for up to eight hours. This is accomplished with comfortable padded straps or a sling with enough freedom of movement to permit the animal to adopt a normal squatting posture above a urinary flow meter during micturition.

Pigs are placed in a prone position. A 5 cm midline back incision is made at the L2–L4 level, and two pockets are created under the skin of each side of the incision to accommodate the port-catheter reservoir. A 60 cm length of tubing is threaded subcutaneously on each side of the abdomen and left under the skin of the lower abdomen to facilitate later identification. The skin of the back is then closed, and the pig moved into the supine position. The bladder is exposed through a midline abdominal incision, and a purse string suture placed at the dome of the bladder.

The two port-catheter tubing lengths already implanted are identified in the incision and threaded through the abdominal wall to reach the bladder and the peritoneum. The right side tubing is cut so that approximately 5 cm lies within the bladder. Three to five lateral holes are made in the end segment and the tubing is inserted through a small incision at the center of the purse string suture. The suture is tied around the tubing to render the bladder watertight. The bladder dome wall is fixed to the abdominal wall fascia with two 3/O chromic gut sutures on each side of the catheter to prevent its displacement. The left side tubing is prepared in the same way but is left lying free in the Pouch of Douglas. The incision is then closed in layers. Animals are housed separately for 5 days and given trimethoprim/sulfa orally, 2.2 mg/kg b.i.d. postoperatively for 5 days.

The back skin covering the subcutaneous ports is anesthetized with 5% EMLA cream; after 15 minutes, the catheter sites are cleaned with an iodine soap, rinsed, and additional iodine applied directly to the sites before puncturing the skin and septum of the port with a 20 g Huber point needle.

A urine sample for culture is drawn from the intravesical port. Needles from both ports are then connected via approximately 1 m long tubing to external pressure transducers positioned at approximately the level of the animal's symphysis pubis. A flow meter is be placed behind and underneath the animal to measure uroflow and voided volume. Diuresis may be induced with 5% furosemide (2.2 mg/kg IM); water is freely available in the restraint device. Alternatively, 0.9% sterile saline at 37° C. may be introduced via the port catheter at approximately 10 to 15 ml/min.

Implantation of Telemetry Device

A telemetry device may be implanted for the recording of intravesical and intraabdominal pressures. The telemetry device (Data Sciences International, St. Paul Minn.;TL11 M3-D70-PCP) has a volume of approximately 33 ml, is roughly circular with a diameter of 56 mm, a thickness of 10–14 mm, and weighs approximately 50 g. Attached to this device are two pressure catheters of 1.2 mm diameter and a length of 25 to 40 cm. The end of each fluid-filled catheter is filled with a biocompatible gel that transmits pressure changes from the surrounding biological environment to the pressure transducer proper. The implant contains a magnetically actuated switch to preserve battery life (warranted for up to 2.5 months of continuous service).

The pressure catheter is implanted in the cranial aspect of the bladder through a 3–4 mm long incision and stabilized with a purse string suture around a plastic anchor located at the end of the catheter to maintain the angle of approach to the bladder. The second transducer tip is left lying free in the Pouch of Douglas. The body of the implant is secured to the muscle of the lateral body wall with silk sutures. The incision is then closed in layers. Animals are housed separately for 5 days and given trimethoprim/sulfa 2.2 mg/kg orally, b.i.d. postoperatively for 5 days. Bladder pressure calibration checks and zero pressure measurements are made by periodic catheterization of the bladder.

Urodynamic Studies and Intravesical Drug Administration.

The efficacy of agents delivered directly to the bladder (to minimize potential side effects compared to systemic administration) is evaluated. Awake animals are catheterized or have a cystoscope inserted into the bladder via the urethra; the tip of the inserted devices will be coated with a local anesthetic cream. Introduction of this device permits direct urodynamic evaluation of bladder function as it is performed in the human clinic, allows direct calibration of other indwelling pressure measurement devices, and permits administration of test compounds by the intended route of administration.

Since one objective of this invention is to reduce systemic side effects of agents delivered directly to the bladder, attempts are made to impair the barrier a function of the glycosoaminoglycan (GAG) layer of the bladder by administering protamine (5 mg/ml, 100 ml), and to restore barrier function by administering heparin (2000 units/mil, 100 ml).

The integrity of the bladder lining is tested by measuring the absorption of fluorescein from the bladder before and after each treatment. For this, fluorescein in concentrations up to 10% is administered to the bladder. These are same concentrations routinely administered to humans intravenously. The absorption of test medications from the bladder is determined systemically before and after protamine treatment. This provides information on the maximum concentrations that can be administered to incontinent patients with impaired GAG layer function, ie. those patients with interstitial cystitis.

Micturition of the animals is measured noninvasively in telemetry experiments or via indwelling bladder cannulae. Some telemetry experiments may be done in the home pen. Filling of the bladder is be accomplished by direct infusion via an indwelling or urethral catheter, by ingestion of preferred liquids, and/or by administration of diuretics before the session. Intravesical and intraabdominal pressures will be recorded, as will the volume and rate of urine production.

Animal Models of Bladder Instability.

Under general anesthesia, a midline laparotomy is performed and a standard circumferential supratrigonal full-thickness bladder transection carried out. The bladder is resutured with a single layer of chromic catgut sutures and two 6F cannulae, or two port catheters, or a telemetry device and a catheter implanted for subsequent urodynamic studies. Animals serving as controls for the cystotomy itself undergo a vertical bivalving of the bladder, the incision extending from the upper margin of the trigone posteriorly to a point approximately 2 cm above the vesicourethral junction anteriorly. The circumferential bladder transection results in bladder instability in approximately 3 weeks, characterized by supersensitivity of the detrusor strips in vitro in the absence or loss of nerve from the detrusor muscle (Sethia et al., *J. Urol* 143:1243–6, 1990). Spontaneous detrusor contractions are observed for 20 days after surgery, while micturition remains intact. This presynaptic denervation model will allow a fuller characterization of agents and a differentiation among agents that show significant promise of clinical utility.

Minipigs tolerate indwelling intravesical and intraabdominal pressure catheters attached to subcutaneous ports (Guan et al., 1994). Another model described by Guan, Z. et al., *J. Urol.* 154:580–586 (1995) is a partial bladder outlet obstruction model. In the obstructed group, an artificial 4.5 cm sphincter cutoff was placed around the bladder neck. 14 of these 21 mini-pigs were eventually deobstructed. In the controls (unobstructed sham-operated group) the sphincter cuff was removed prior to closure. Urodynamic measurements conducted at 2, 4, 8, and 12 weeks postobstruction in conscious animals restrained in specially designed adjustable cages indicated a reversible infravesical obstruction gave consistent and reproducible pressure flow data when animals were in a conscious upright state.

Correlation of the rank order of potency for muscarinic antagonism between mini-pigs and guinea pigs (Peterson, J. S., et al.,*Auton. Pharmac.* 10:65–73 (1990)) has been shown to be very high in vitro ($R=0.97$, $P<0.05$) as was the correlation among the drugs for their ability to depress $P_{ves}P$ of the cystometrogram in vivo ($R=0.89$, $P<0.05$). These studies employed carbachol-induced contractions on mini-pig bladder tissue strips in vitro and demonstrated that antagonist drugs produced a rank order of potency similar to that observed in guinea pig tissues. The drugs appeared to show competitive antagonism and the tissues exhibited resistance to complete cholinergic blockage. Cytometry performed in vivo on awake mini-pigs also showed that i.v. cholinergic antagonists produced a dose-dependent depression of peak intravesical bladder pressure ($P_{ves}P$) during slow filling of the bladder using urethral catheters, with a rank order of potency: atropine>oxybutyin.propantheline>HHSiD.dicyclomine>terodiline. Other parameters of the cystometrogram were unaffected by the antagonists, except for residual volume, was generally increased after drug treatment. Hexahydrosiladifenidol (HHSiD), an ileum-selective competitive muscarinic antagonist, was about as effective an antagonist as the clinically useful oxybutynin or dicyclomine, both in vitro and in vivo. These results showed a strong similarity between muscarinic receptors and their actions in mini-pig and guinea pig urinary bladder tissues. These species are therefor useful in examining drug therapies to treat urinary incontinence for widely different classes of chemical compounds including calcium antagonists, tricyclic antidepressants in addition to cholinergic antagonists.

Screening: Comparison to Standards

Intravesical administration is the preferred route of administration for the present invention. When evaluating compounds, however, intravenous administration is used to provide benchmarks for the comparison of anticholinergic side effects which the intravesical route is intended to avoid. Thus heart rate, rectal temperature, or measures of dry mouth (e.g., superficial cannulation of the submaxillary salivary gland) are evaluated and compared with the doses necessary to alter detrusor function.

Comparisons are then made between the intravesical administration protocol, which is designed to mimic one of two clinical situations, and an immediate assay of altered detrusor function (treat-to-effect), The two clinical situations are: (1) patient administered clean intermittent catheterization (single instillation) model and (2) outpatient procedure using continuous perfusion with known concentration of drug. In the instillation model, it is possible to obtain simultaneous measurements of drug disappearance from the bladder lumen, i.e., absorption. The "treat-to-effect" approach is a very appealing model and is likely to produce clinically acceptable effects while minimizing the risk of adverse side effects due to unnecessarily prolonged instillation times or unnecessarily elevated doses.

Thus a prototypical evaluation entails administration of a solution of the agent, e.g., a 4-DAMP bromo mustard, by continuous intravesical infusion until a reduction in peak intravesical pressure occurs comparable to that produced by an optimal dose of oxybutynin administered by two routes. By the intravenous route, side effects will be demonstrable. The duration of action of the test thus becomes the key outcome measure and is the basis for determining the utility of an agent as having no detectable side effects (or acceptably low side effects) in combination with prolonged duration of action compared to the current conventional drugs.

Identification of Individuals at Risk for Side Effects

To identify subjects at risk for persistent side effects as a result of abnormally high absorption of chemicals across the bladder wall (e.g., subjects with interstitial cystitis or inadequate GAG production or adherence, the following approach is used. Fluorescein (or another detectable label or marker) is administered to the bladder, and its disappearance measured in situ by the appropriate means. In the case of fluorescein or other fluorescent markers, spectrofluorimetry is used. Disappearance rates are evaluated both in a closed recirculation mode through the flowthrough cell of the spectrofluorimeter, or in an open single compartment exponential dilution mode. Thus abnormally high rates of absorption from the bladder can be detected in an initial ten minute procedure before the administration of the antimuscarinic agent.

In an animal model of this measurement, the GAG layer of the bladder is disrupted and partially restored as described above.

The same methods are applied to human subjects to examine the utility of this approach in the context of managing patients with interstitial cystitis, either by following individuals in within-patient sequential designs, or in the assignment of patients to groups for clinical trials evaluating different intervention strategies.

A pharmaceutical composition which combines heparin or other GAGs with the antimuscarinic agent of this invention is thought to minimize the variability in absorption between individuals and possibly to prolong duration of action of the drug.

Treatment of Bladder Disease

The administration of novel antimuscarinic agents via a catheter to the bladder will result in prolonged maintenance of bladder control in otherwise incontinent patients. The antimuscarinic compounds that are useful in this regard are preferably those quaternary agents with reactive moieties, quaternary and nonquaternary compounds with very high affinities for the $M_3$ muscarinic receptor, large molecules that are poorly absorbed but retain some receptor affinity, and compounds that tend to be retained in the glycosoaminoglycan layer of the bladder from which they may partition slowly into the detrusor muscle and adjacent receptor sites. This invention includes not only known compounds that have not been recognized as having such utility, but also compounds yet to be synthesized that have the properties set forth above.

These pharmaceutical compositions are preferably administered by the intravesical route. The present invention also provides special kits useful for the preparation, administration, and quantification of effectiveness of drug delivery for individual patients.

In addition, the compositions and methods of the present invention are useful in the treatment of any disease or condition which is advantageously treatable with an irreversible antimuscarinic agent administered primarily locally or regionally, even if some of the agent becomes systemically distributed.

The preferred animal subject of the present invention is a mammal. The invention is particularly useful in the treatment of human subjects.

A pharmaceutical composition of the present invention comprises the antimuscarinic compound as described above and a pharmaceutically acceptable carrier or excipient.

In one embodiment, the pharmaceutical composition comprises an irreversible antimuscarinic agent in combination with another medicament useful in treating one or more symptoms of the disease. Medicaments are considered to be provided "in combination" with one another if they are provided to the patient concurrently or if the time between the administration of each medicament is such as to permit an overlap of biological activity.

The pharmaceutical composition of the present invention may be administered by any means that achieves its intended purpose. Amounts and regimens for the administration of the composition can be determined readily by those with ordinary skill in the clinical art of treating bladder diseases with assays and techniques such as those described herein.

In addition to intravesical administration, the compounds of the invention or other medicaments which are given in combination, may be by subcutaneous, intravenous, intramuscular, intraperitoneal, transdermal routes. Alternatively, or concurrently, administration may be by the oral route.

The route and the dosage administered will be dependent upon the age, health, and weight of the recipient, kind of concurrent treatment, if any, frequency of treatment, and the nature of the effect desired.

Compositions within the scope of this invention include all compositions wherein the irreversible antimuscarinic compound is contained in an amount effective to achieve its intended purpose. While individual needs vary, determination of optimal ranges of effective amounts of each component is within the skill of the art. Typical dosages of the active compounds comprise 1 pg/kg/body wt. to 100 mg/kg/body wt. The preferred dosages comprise 0.001 to 10 mg/kg/body wt. The most preferred dosages comprise 0.01 to 1 mg/kg/body wt. For intravesical administration, doses expressed in mass of drug per subject or cumulative dose as mass per subject are more appropriate. Preferred dosages are in the range of 1 pg to 10 mg per subject per treatment, more preferably 1 ng to 1 mg per subject.

In addition to the pharmacologically active compound or compounds, the pharmaceutical composition preferably contains one or more suitable pharmaceutically acceptable carriers comprising excipients and auxiliaries which facilitate processing of the active compounds into preparations which can be used pharmaceutically. Most preferred are suitable solutions for administration by intravesical instillation and which contain from about 0.01 to 99 percent, preferably from about 20% to 75% of active compound(s), together with the excipient.

Suitable formulations for administration include aqueous injection solutions which may contain antioxidants, buffers, bacteriostats, and other additives commonly employed in such solutions. The active compounds are preferably in water-soluble form, for example, as water-soluble salts, in particular acid or base addition salts, for example, hydrochlorides or hydrobromides. Alternatively, suspensions of the active compounds as appropriate may be administered. Aqueous suspensions may contain substances which increase the viscosity of the suspension, for example, sodium carboxymethyl cellulose (CMC), sorbitol, and/or dextran. For example, intravesical administration of oxybutynin with CMC prolonged the drug's action by about 3-fold.

A number of GAGs have been administered intravesically including heparin and pentosan sulfate (Elmiron®). Since lining of bladder is replete with GAGs, inclusion of GAGS may provide the same effects as CMC noted above. Material that promotes the uptake of the drug into the bladder lining would improve the time course of its contact with the bladder wall and is desirable.

As noted above, in other embodiments, the treatment comprises aministering a mixture of GAGs with the antimuscarinic compound following protamine treatment. Altnerantively, GAG substituents may be utilized.

Other pharmaceutically acceptable carriers for the antimuscarinic compositions of the present invention are liposomes, pharmaceutical compositions in which the active agent is contained either dispersed or variously present in corpuscles consisting of aqueous concentric layers adherent to lipidic layers. The active agent is preferably present in the aqueous layer and in the lipidic layer, inside or outside, or, in any event, in the non-homogeneous system generally known as a liposomic suspension. The hydrophobic layer, or lipidic layer, generally, but not exclusively, comprises phospholipids such as lecithin and sphingomyelin, steroids such as cholesterol, more or less ionic surface active substances such as dicetylphosphate, stearylamine or phosphatidic acid, and/or other materials of a hydrophobic nature.

Possible Mechanisms of Action

Several mechanisms may account for the irreversibility of the antimuscarinic properties of the compositions of this invention, although the inventors do not wish to be bound by any particular mechanism or mechanisms of action.

It is postulated that the irreversibility of the biological effect results from the formation of a ligand-receptor complex of the compound and the muscarinic receptor, preferably the $M_3$ receptor, followed by the formation of a covalent hydrogen bond between a moiety of the compound with a site on the adjacent membrane surface.

Despite the substantial irreversibility of some of the agents described herein, receptor turnover would be expected to counteract the agents' duration of action. Although one would expect prompt relief, an agent with prolonged effects has particular utility for painful or inconvenient routes and forms of administration. This is particularly evident in the case of intravesical instillation. Thus, the compositions and methods of this invention have an advantage over other drugs or other routes of administration. Furthermore, these agents, would be less likely to induce overuse tolerance or toxicity. Moreover, long-acting antimuscarinic agents such as the compounds described herein, all of which were previously not available, or, alternatively, not contemplated nor described in the literature for this purpose, would be particularly suitable for the treatment of bladder disease.

Administration of the Therapeutic Compositions and Measurement of Bladder Wall Permeability Systemic absorption of compounds is possible from the bladder, and can be enhanced by some disease conditions, e.g. interstitial cystitis (Parsons, C L et al *J. Urol.* 145:732–735 (1991)), wounds or other conditions associated with increased permeability of the bladder wall. Therefore, it is important to demonstrate the absence of systemic side effects when using the present compositions and methods for intravesical therapy. Using methods described herein as well as conventional techniques, one can test the safety of an irreversible anticholinergic composition under these conditions. The present inventor has also devised new techniques for rapid determination of the permeability of the bladder wall.

One such technique utilizes dyes such as fluorescein or indocyanine green instilled intravesically. Dyes leaking through a weakened bladder wall will disappear from the lumen and be taken up into the circulation more readily and can be detected at a distance, for example intraocularly by fundoscopic examination reaching the skin by a dermatofluorimeter.

It is therefore possible to measure disappearance from the intravesical space (see below) or by direct measurements, e.g., in the blood. In patients with interstitial cystitis, such methods may predict which patients experience side-effects from a known or novel compound given intravesically for the treatment of the bladder disease.

A fluorescent markers or a fluorescenty-tagged therapeutic agents (e.g., a fluorescein isothiocyanate-labeled anticholinergic agents) is administered during treatment of bladder instability to provide alternate criteria for the cessation of drug treatment. Such techniques are also useful with other drugs such as antineoplastic agents, and with agents given by other routes where absorption is variable or unpredictable. Measurement may be achieved transcutaneously or intraocularly as noted above, and can also incorporate the use of secondary wavelengths as a control for fixation or background fluorescence. Any fluorescent compound can be used for this purpose.

Measurement of Clinical Effects

Standard methods are used to assess the efficacy of an agent, dose or therapeutic regiment. Improvements in subjective parameters of urge incontinence such as urinary frequency or urgency are shown to improve with the compositions and methods disclosed herein. Also seen to improve are objective cystometric measures including maximum detrusor pressure during filling, volume at first desire to void and maximum bladder capacity.

Improvements in comparison to other therapeutic agents of the same category, such as oral oxybutynin, propantheline and propiverine is a further way in which the clinical efficacy of the present invention is measured.

The chief advantage of the present compounds and methods is that the frequency of instillation can be reduced significantly. As an example in a study of children with myelomeningocele, patients were given intravesical oxybutynin twice daily for a minimum of 4 months (Connor J P et al., *J. Urol.* 151:1045–1047 (1994). The mean bladder capacity increased by 41%, the mean intravesical pressure decreased by 47% and compliance improved. Five of 28 patients achieved continence and 62% had less wetting while on intravesical therapy. With the present invention, similar results may be achieved with intravesical instillation at a frequency of between once a week to once in four weeks. The poor compliance found after follow-up in the Connor et al. study (15 of 28 patients dropped out during the four month the duration) is indicative of the problems associated with multiple daily instillation of drugs into the bladder and further points out the significance of the present invention.

The compositions and methods described herein provide therapeutic approaches to different patient groups ranging from inpatients requiring more frequent therapy with assistance, to outpatients who can self-administer the drugs with the aid of kits that are also included within the scope of this invention. These kits are for carrying out the method of this invention and for employing the compositions. Thus, a preferred kit comprises the antimuscarinic drug, alone or in combination with other agents, as above, and formulated for intravesical instillation. Also included in the kit are the equipment and disposable supplies needed for intermittent sterile or clean self catheterization. Kits containing syringes, tubing, etc. for such uses are well-known in the art and commercially available. The present invention provides the long acting agents that treat incontinence and other bladder diseases. The kits preferably also contain instructions on the use of the drugs in conjunction with the equipment for intravesical administration.

Having now generally described the invention, the same will be more readily understood through reference to the following examples which are provided by way of illustration, and are not intended to be limiting of the present invention, unless specified.

EXAMPLE I

Guinea Pig Bladder Study with Oxybutynin

A course of treatment with oxybutynin administered either intravenously or intravesically was studied. The results appear in FIGS. 3A, 3B and 4.

Guinea pigs were anesthetized with 15% (w/v) urethane solution (1.5 g/kg body weight i.p.). The anesthetized guinea pigs were placed supine on a heated pad and their bladders catheterized via the urethra with PE150 tubing. The urethral opening was tightly sutured to prevent leakage during the filling phase. The tubing was attached to a pressure transducer, a syringe pump for bladder filling, and an exit port to empty the bladder between trials. The bladder was filled at a constant rate until a coordinated and sustained contraction occurred. The bladder was then drained, a five minute rest period ensued, and the cycle was repeated.

In one experiment, animals were injected IV and their responses to various doses of oxybutynin measured. Results shown in FIGS. 3A and 3B indicate that doses of about 1 mg/kg resulted in a significant fall in peak intravesical pressure and a related increase in volume.

In another study, a solution of oxybutynin at a concentration of $10^{-3}$M was administered intravesically at a rate of 0.5 ml/min. Drug administration was initiated 85 minutes into the study and resulted in an almost immediate fall of about 70% in peak intravesical pressure Preparations of this type are the "first-tier" screen for compounds thought to have promise for the treatment of incontinence Larger animal models, such as swine (see below) have achieved a high degree of refinement in practice, and have been utilized extensively, and in preference to other preparations.

EXAMPLE II

Studies of Bladder Function in Miniature Swine

The following describes the procedures and results in the study of bladder function in miniature swine. Most of these procedures have been carried out in the studies that yielded FIGS. 5A–5E.

Implantation of Port-Catheters

Pigs are placed in a prone position. A 5 cm midline back incision is made at the L2–L4 level, and then two pockets are created under the skin of each side of the incision to accommodate the port-catheter reservoir. A 60 cm length of tubing is threaded subcutaneously on each side of the abdomen and left under the skin of the lower abdomen to facilitate later identification. The skin of the back will then be closed, and the pig moved into the supine position, the bladder exposed through a midline abdominal incision, and a pursestring suture placed at the dome of the bladder. The two port-catheter tubing lengths already implanted are identified in the incision and threaded through the abdominal wall to reach the bladder and the peritoneum. The right side tubing is cut so that approximately 5 cm will lie within the bladder. Three to five lateral holes are made in the end segment and then inserted through a small incision at the center of the pursestring suture; the suture will then be tied around the tubing to render the bladder watertight. The bladder dome wall is fixed to the abdominal wall fascia with two 3/0 chromic catgut sutures on each side of the catheter to prevent its displacement. The left side tubing is prepared in the same way and left lying free in the Pouch of Douglas. The incision will then be closed in layers. Animals are housed separately for 5 days and given trimethoprim/sulfa orally, 2.2 mg/kg b.i.d. postoperatively for 5 days.

Animal Model of Bladder Instability

Under general anesthesia a midline laparotomy is performed and a standard circumferential supratrigonal full-thickness bladder transection carried out. The bladder is resutured with a single layer of chromic catgut sutures and two 6F cannulae, or two port catheters, or a telemetry device and a catheter implanted for subsequent urodynamic studies. Animals serving as controls for the cystotomy itself undergo a vertical bivalving of the bladder, the incision extending from the upper margin of the trigone posteriorly to a point approximately 2 cm above the vesico-urethral junction anteriorly. The circumferential bladder transection results in bladder instability in approximately 3 weeks, characterized by supersensitivity of the detrusor strips in vitro in the absence of loss of nerve from the detrusor muscle (Sethia et al., *J Urol* 143:1243–1246, 1990).

Urodynamic Studies Using Port-Catheters.

Awake animals walk into a restraint stock, squeeze cage or sling suitable for use with swine and ruminant species, and are restrained in an upright standing position for up to eight hours. This is accomplished with comfortable padded straps or a Panepinto sling with enough freedom of movement to permit the animal to adopt a normal squatting posture above a urinary flow meter during micturition.

The back skin covering the subcutaneous ports is anesthetized with 5% EMLA cream; after 15 minutes, the catheter sites are cleaned with an iodine soap, rinsed, and additional iodine applied directly to the sites before puncturing the skin and septum of the port with a 20 g Huber point needle.

A urine sample for culture is drawn from the intravesical port. Needles from both ports are then connected via approximately 1 m long tubing to external pressure transducers positioned at approximately the level of the animal's symphysis pubis. A flow meter is placed behind and underneath the animal to measure uroflow and voided volume. Diuresis may be induced with 5% furosemide (2.2 mg/kg IM); water is freely available in the restraint device. Alternatively, 0.9% sterile saline at 37° C. is introduced via the port catheter at approximately 10 to 15 mi/min. Sixty studies may be carried out per animal.

Urodynamic Studies and Intravesical Drug Administration.

Agents are tested by delivery directly to the bladder in order to minimize side effects that are more likely when the drugs are administered systemically. Awake animals are catheterized or may have a cystoscope inserted into the bladder via the urethra in a more acute setting. The tip of the inserted devices is coated with a local anesthetic cream. Introduction of this device permits direct urodynamic evaluation of bladder function the same way it is performed in the human clinic, thereby allowing direct calibration of other indwelling pressure measurement devices, and administration of test compounds by the intended route of administration.

Since one objective of this invention is the reduction of systemic side effects of agents delivered directly to the bladder, attempts are made in certain studies to impair the barrier function of the glycosoaminoglycan (GAG) layer of the bladder by giving protamine (5 mg/ml, 100 ml), and to restore its function by giving heparin (2000 units/ml, 100 ml).

The integrity of the bladder lining is studied by measuring the absorption of fluorescein from the bladder before and after each treatment as discussed in Example IV; fluorescein is be administered to the bladder in concentrations up to 10%, the same concentrations routinely administered to humans intravenously. The absorption of test medications from the bladder is determined systemically before and after protamine treatment in an attempt to determine the maximum concentrations that can be administered to incontinent patients with impaired GAG layer function, i.e. those with interstitial cystitis. A maximum of 60 studies per animal is anticipated.

Core Studies

The core studies examine cumulative within-session dose-effects of the drugs on various functions. A flow rate of 20 ml/min of saline results in filling of the approximately 200 ml capacity of the bladder. Therefore 6 determinations are made per hour, and with 6 one hour sessions, 36 data points are generated per pig per day. At minimum, two replications are performed per dose or agent. Comparisons are made with cumulative effects with single dose per session or with IV bolus doses.

Results

FIG. 5A–5E presents data collected from a typical swine cystometry session. The top panel (5A) presents intravesicular ($P_{ves}$) and intraabdominal ($P_{abd}$) pressure, and the difference ($P_{det}$) between these two. (The right axis is for the intraabdominal pressure). The simultaneous recording of these two pressures permits distinguishing between contractions of the bladder and pressure in the bladder created by valsalva movements or vocalization. A good example of this is the 10 mm Hg pressure event in the bladder at 11:30 in the top panel: this was a true bladder contraction. Note that the magnitude of the motion artifacts in the $P_{det}$ are reduced in comparison to $P_{ves}$ as a result of the subtraction.

Figure 5A:
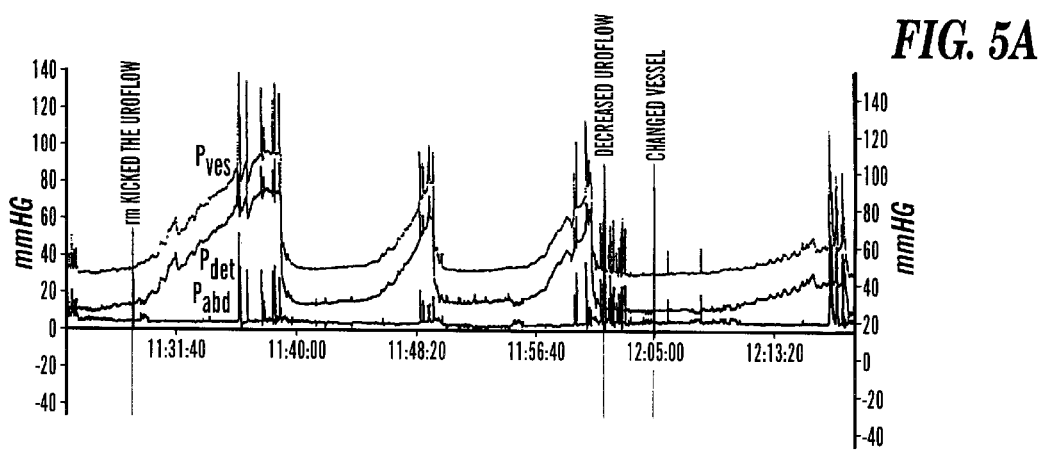
Figure 5B:
Figure 5C:
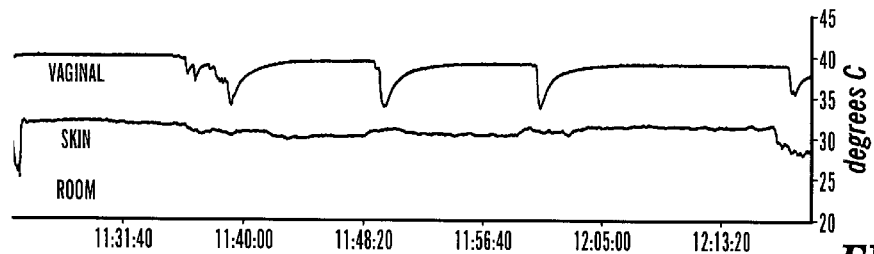
Figure 5D:
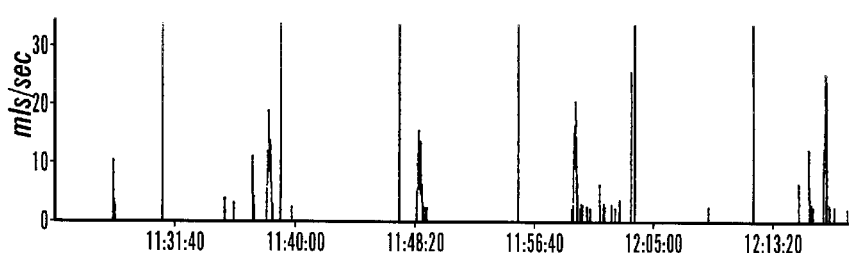
Figure 5E:
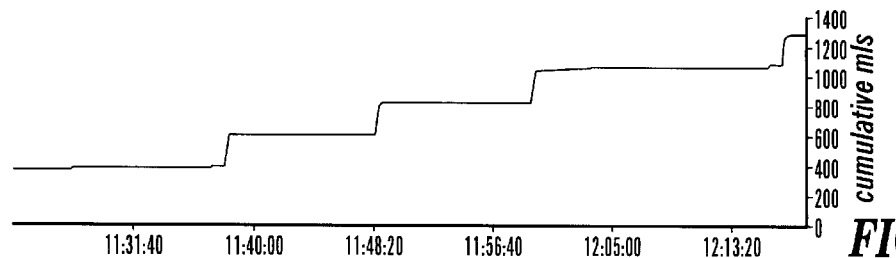

FIG. 5B is the raw data signal from the transducer. FIG. 5D displays the signal after noise filtering. FIG. SE shows the integrated total flow across the session. FIG. 5C shows the skin and vaginal temperatures throughout the study. Mechanical artifacts can also occur in the measurement of urine flow (uroflow) and two are obvious in this session. At approximately 11:29, one investigators bumped the uroflow transducer, producing a spike (FIG. 5b, which is the raw data signal from the transducer. The lower panel displays the signal after noise filtering, as well as the integrated total flow across the session. Note that the artifact resulted in a very small volume estimate, both then and at 12:05 when the uroflow container was changed. There can be no mistaking these flows for genuine micturition however, since the vaginal temperature measurement clearly indicates a drop in temperature as the animal voids cool saline into the vagina. These temperature drops provide additional verification at to when integrated urine volume estimates are accurate.

The voided volume was approximately 200 mls for each of the three voids depicted. The flow rate was reduced from 20 mls/min to 10 mls/min in the final portion of this session, and this was associated with an approximate doubling of the latency to onset of micturition, from 10 to 20 minutes.

The residual volume was measured immediately following these recordings, and was approximately 18 mls. Both these estimates of functional capacity and residual volume are appropriate for animals of this size from the published literature (Guan A et al., supra)

EXAMPLE III

Effects of Antimuscarinic Drugs on Bladder Function in Miniature Swine

Studies such as those described above are performed in animals being treated with drugs of the present invention. Comparisons are made between drugs, between routes of administration, e.g., intravenous. intravesical. Comparisons may be based on the drug dose that achieves a desired clinical or pharmacological effect. Table 1 below shows the predicted results of a study in which either oxybutynin or MeQNB is administered at the doses indicated via the IV route as compared to direct instillation into the bladder (via the implanted ports described above).

Two interdependent bladder functions are measured.: peak intravesical pressure and residual bladder volume. Two physiological activities subject to cholinergic regulation are examined as a measure of undesired side effects: heart rate and body temperature, both of which are known to increase under the influence of antimuscarinic drugs.

TABLE 1

Predicted Effects of Antimuscarinic Therapies - Comparison of Drugs and Intravenous vs. Intravesical Administration

| Drug/Route | Dose µg/pig | Peak intravesical pressure % Decrease | Resid. bladder vol. % Increase | Heart rate % increase | Body Temp increase ° C. |
|---|---|---|---|---|---|
| Oxybutynin | 100 | 0 | 0 | 0 | 0 |
| IV | 1000 | 0–10 | 0–10 | 0–10 | 0.5–1 |
|  | 10,000 | 30–70 | 30–50 | 40–50 | >2 |
| Oxybutynin | 1 | 0 | 0 | 0 | 0 |
| Intravesical | 10 | 0–10 | 0–10 | 0 | 0 |
|  | 100 | 30–70 | 30–50 | 0 | 0 |
| MeQNB | 10 | 0 | 0 | 0 | 0 |
| IV | 100 | 0–10 | 0–10 | 0–10 | 0.5–1 |
|  | 1000 | 30–70 | 30–50 | 40–50 | >2 |
| MeQNB | 0.1 | 0 | 0 | 0 | 0 |
| Intravesical | 1 | 0–10 | 0–10 | 0 | 0 |
|  | 10 | 30–70 | 30–50 | 0 | 0 |

As the results will show, MeQNB is about 10-fold more active than oxybutynin by either route. As expected, the agents are about 100-fold more active (dose-to-effect) intravesically vs. IV. Finally, none of the doses given intravesically will have any measurable side effects. Thus, effective doses by direct intravesical instillation are free of side effects.

Actual experimental results of studies by the present inventor using oxybutynin shoed that intravsecial administration produced an effect, increased duration of micturition, which was followed by recoery during continuous intravsical perfusion. This is consistent with a decrease in the force of muscle contraction. However, the sphincters have opened, so the muscle is not contracting against a resistance other than the urethra. A test with outlet obstruction (e.g., intravaginal finger on the urethral opening) or, as the inventor has studied in guinea pigs, where pressure is released after the muscle contracts and reaches its peak, clearly produced this effect. In any event, with the methods of the present invention, the duration of the micturition event is likely to increase.

Examination of other agents for duration of action in this model will also show the prolonged actions of quaternary antimuscarinic compounds disclosed herein as well as of compounds attached to bulky side chains.

EXAMPLE IV

Quantitative Fluorescence Cystoscopy/Cystometry

Tubing within the light path must be transparent; PVC IV extension sets are suitable since they come with internal surfaces sterile. Two lengths are placed inside a cassette for insertion into the light path of the instrument. The instrument light path is protected from any contamination by room illumination. Calibration solutions are placed in a syringe or funnel and are passed through the light path adjacent to the tubing through which the bladder contents are pumped.

PharmMed #14 tubing is used in the Masterflex peristaltic pump incorporated in existing clinical instruments for cystoscopy. This tubing material can be autoclaved repeatedly without degradation. Such tubing is also available packaged in a 4 foot length with permanent Luer-lok adapters.

Connection from the cystoscope or catheter to the spectrofluorimeter is done with a pair of PharMed tubing lengths which has the advantage of being opaque. Alternatively, two four foot lengths of extension tube with Luers on both ends are used.

In the cystoscope configuration, an infant feeding tube or similar blunt tipped catheter is introduced through the instrument port to provide some distance between the inlet and outlet points within the bladder, thus insuring adequate mixing of the fluorescent solution.

The entire setup uses disposable materials for infection control. The system is all Luer Lock®, 2 each of the following: 20 inch extensions for the optical path; 42 inch extensions for the segment between the cystoscope and the fluorimeter; three-way stopcocks.

One possible exception is the tubing which is inserted in the peristaltic pump. Some pumps have prepackaged sterile tubing lengths, and these may be unnecessarily expensive. For a pump of the Masterflex type, we PharmiMed® tubing is cut packaged for the autoclave; each length is attached with a pair of luer-to-hose barb fittings. This tubing can be discarded, unless a filter bed is placed in line to remove any shed detritus from the circuit.

This device is brought into an operating room or urology outpatient clinic. Software is used to generate a calibration curve and do the calibration linear regression analysis.

Custom Spectrofluorometer Using Sterile Extension Sets as Cuvettes

This instrument was contructed in the University machine shops from drawings that the inventor and his colleagues prepared. Photographs of the instrument are presented in FIG. 6A. A 21VDC regulated light source (A20760.2) and fiber optic cable were obtained from (Fostek, Auburn, N.Y.). An optimal pair of digital grating filters were purchased from Chroma Technology Corp (Brattleboro,Vt.): the excitation filter HQ485/30; the barrier filter D550/50. The light output of the barrier filter was further reduced with a Kodak Number 2 ND neutral density filter. This was located in from of a Hamamatsu photomultiplier tube energized by a regulated high voltage supply. The output was measured across a one megohm resistor to reduce current through the tube to less than one milliamp. The fluorescence is so intense that sensitivity is not an issue. This voltage is monitored (as well as associated fluid pressures) with a Dell Pentium II computer system. Data collection is performed with a custom application developed using Labview (National instruments). The data analysis is conducted in RS/1 (BBN Software). Both of these software environments exist within the Windows NT4.0 operating system.

Allegiance Health Care formulates custom sterile cystoscopy research packs. These are opened at the time of the procedure and attached to 2 sterile pressure transducers (Abbot Transpac IV list #42582-05), a sterile female Luerlok to hose barb adapter, and a sterile 10 inch length of Pharmed L/S 25 tubing (Cole-Parmer Instruments Co.) The pressure transducers are placed between the short and long extension sets on either end of the assembly. The kits contain: 2 infant feeding tubes (8 and 10 Fr), 15 in long; 3×20 in extension sets; 2×6 in extension sets; 3×35 in extension sets; 3 three-way stopcocks; a 19 GA×1.5 inch filter needle with 5 micron filter.

The parts are assembled in the following order: Infant feeding tube (8 and 10 French, 15" long) fed through;

Rubber collar/septum on instument port of cystoscope short (6") extension set pressure transducer long (35") extension set three-way stopcock attached to a 35" extension set (to drain) three-way stopcock (Filling port)

three-way stopcock (Filling port)

Female Luer lock to hose barb adapter

Pharmed L/S 25 tubing for peristaltic pump medium (20") extension set (for spectrofluorometer)

long (35") extension set
pressure transducer
short (6") extension set

EXAMPLE V

Instillation of Dye for Measurements

In humans, approximately 200 mls of a 1 ppm solution is instilled into the bladder. About 50% is absorbed by some patients over ten minutes. Thus the total dose of the fluorescein dye is 1/1000th or less of the amount used routinely in fundus photography—fluorescein angiography (in ophthalmologic practice). The highest concentration used is 3 ppm for disappearance studies. Higher amounts are used if no residual fluorescence can be observed in the bladder wall in cystitis or cancer patients.

A light bench with the appropriate filters is used to measure a concentration-related signal at the output of a photomultiplier tube.

EXAMPLE VI

AEME has Anticholinergic Activity In Vitro

Guinea pig detrusor contractions were studied in vitro using the methods of E1 Fawal and Wood (supra). AEME at $10^{-6}$M, after 5 mim of incubation, reduced response of tissue to $10^{-4}$M ACh. This attenuation was not reversed after 45 min of washing at 10 minute intervals. This experiment was systematically repeated by examining the response of the tissue to a range of ACh concentrations (up to $2 \times 10^{-3}$M), (a) alone, (b) in the presence of $10^{-7}$M AEME and (c) following a 75 min washout.

The respone to ACh was again attenuated without change in the threshold at which ACh elicited a response to AEME, and did not recover after repreated washings.

These effects are similat to the findings using tracheal rings. Antimuscarinic properties of AEME on tracheal rings were observed at levels as low as $10^{-9}$ M. AEME at $10^{-7}$ M reduced the sensitization to ACh produced by cocaine at $5 \times 10^{-6}$ M.

In both tissues, the dominant muscarinic receptor subtype is $M_3$. The effects observed are consistent with non-competitive irreversible antagonism of ACh.

EXAMPLE VII

Systemic Administration of AEME In Vivo

AEME administered by the intravenous and inhalation routes in primates yielded results in the lung consistent with the in vitro studies of tracheal rings with respect to anticholinergic effects. In fact, the in vivo effects were more sustained and dramatic than anticipated based on the in vitro results. It is noteworthy that AEME had a wide margin of safety in these studies.

The references cited above are all incorporated by reference herein, whether specifically incorporated or not.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the invention following, in general, the principles of the invention and including such departures from the present disclosure as come within known or customary practice within the art to which the invention pertains and as may be applied to the essential features hereinbefore set forth as follows in the scope of the appended claims.

What is claimed is:

1. A method for treating bladder disease in a subject, comprising:
   administering to the bladder of said subject an effective amount of a composition that comprises a chemical compound having the following properties:
   (a) binds selectively to muscarinic receptors in the bladder when compared to non-muscarnic receptors;
   (b) is a glycolate ester of a heterocyclic amino alcohol of the general formula

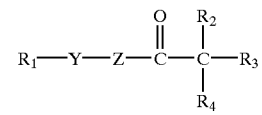

or a salt thereof, wherein
   $R_1$ is a heterocyclic N-substituted ring;
   Y is a chemical bond or a lower alkyl group;
   Z is O or S;
   $R_2$ is OH, Cl, an acyl alcohol group or an acyl chloride group;
   $R_3$ and $R_4$ are, independently, a substituted or unsubstituted phenyl, a substituted or unsubstituted cycloalkyl, a straight or branched chain alkyl, alkenyl or alkynyl, and further, one of $R_3$ and $R_4$ may be H
   with the proviso that said compound is not a quinuclidinyl derivative, glycopyrrolate, or trospium chloride.

2. A method according to claim 1 wherein said N of $R_1$ is a quaternary N.

3. A method according to claim 1, wherein $R_2$ is OH.

4. A method according to any one of claims 1–3 wherein the heterocyclic ring is selected from the group consisting of 3-piperidinyl, 4-piperidinyl, 3-pyrrolidinyl, 3-quinuclidinyl, 3-granatanyl, 3-tropinyl, 3-granatanyl epoxide and 3-tropinyl epoxide.

5. A method according to claim 2, wherein said quaternary nitrogen atom is substituted with a straight or branched $C_1$–$C_{10}$alkyl, alkenyl, alkynyl, substituted alkyl, substituted alkenyl, substituted alkynyl or an amidine.

6. A method according to claim 5 wherein said quaternary nitrogen atom is derivatized with a methyl or isopropyl group.

7. A method according to claim 2 wherein:
   $R_1$ is an N-methyl-4-piperidyl ring; Y is a chemical bond or $CH_2$; Z is O; $R_2$ is OH; and $R_3$ and $R_4$ phenyl and cyclobutyl.

8. A method according to claim 2 wherein:
   $R_1$ is an N-methyl-4-piperidyl ring; Y is a chemical bond or $CH_2$; Z is O; $R_2$ is OH; and $R_3$ and $R_4$ phenyl and cyclopentyl.

9. A method according to any one of claims 1–3 wherein $R_1$ is 4-piperidinyl in which the N is substituted with X'; $R_2$ and $R_4$ are any of phenyl, cyclohexyl or cyclopentyl; and $R_3$ is H, wherein X' is an optionally halogenated lower alkyl group.

10. A method according to claim 9 wherein X is bromoethyl or bromopropyl.

11. A method according to claim 9, wherein the ring N is quatemized by substitution with a straight or branched $C_1$–$C_{10}$ alkyl, alkenyl, alkynyl, substituted alkyl, substituted alkenyl, substituted alkynyl or an amidine.

12. A method according to claim 1 wherein said compound is additionally substituted with a reactive or alkylating function on any one of $R_1$, $R_2$, $R_3$ or $R_4$.

13. A method according to claim 12 wherein $R_1$ is a heterocyclic N-substituted ring and said reactive or alkylating function is a substituent on the quaternary nitrogen group of said ring.

14. A method according to claim 12 wherein (i) $R_1$ is a heterocyclic N-substituted ring, and, (ii) said reactive substituent is on a ring carbon atom and produces, by spontaneous cyclization in solution, said alkylating function.

15. A method according to claim 14 wherein said alkylating function is an aziridinium ion.

16. A method according to claim 1, wherein said disease is urge incontinence or interstitial cystitis and said administering is by intravesical instillation.

* * * * *